(12) United States Patent
Fernando et al.

(10) Patent No.: US 6,661,512 B2
(45) Date of Patent: Dec. 9, 2003

(54) SAMPLE ANALYSIS SYSTEM WITH FIBER OPTICS AND RELATED METHOD

(75) Inventors: C. J. Anthony Fernando, Durham, NC (US); James E. Swon, Chapel Hill, NC (US)

(73) Assignee: Varian, Inc., Palo Alto, CA (US)

( * ) Notice: Subject to any disclaimer, the term of this patent is extended or adjusted under 35 U.S.C. 154(b) by 17 days.

(21) Appl. No.: 10/076,316

(22) Filed: Feb. 13, 2002

(65) Prior Publication Data

US 2003/0151743 A1 Aug. 14, 2003

(51) Int. Cl.[7] .............................. G01J 3/42; G01N 21/25
(52) U.S. Cl. ........................................ 356/319; 356/436
(58) Field of Search ................................ 356/319, 323, 356/325, 326, 328, 436

(56) References Cited

U.S. PATENT DOCUMENTS

| | | | |
|---|---|---|---|
| 3,697,185 A | * 10/1972 | Kassel et al. | ............... 356/410 |
| 4,431,307 A | 2/1984 | Suovaniemi | |
| 4,528,159 A | 7/1985 | Liston | |
| 4,989,932 A | 2/1991 | Landa et al. | |
| 5,112,134 A | 5/1992 | Chow et al. | |
| 5,210,590 A | * 5/1993 | Landa et al. | ................ 356/319 |
| 5,526,451 A | 6/1996 | Cahill et al. | |
| 5,580,784 A | 12/1996 | Berndt | |
| 5,715,173 A | 2/1998 | Nakajima et al. | |
| 5,804,453 A | 9/1998 | Chen | |
| 6,002,477 A | 12/1999 | Hammer | |
| 6,151,111 A | 11/2000 | Wechsler | |
| 6,174,497 B1 | 1/2001 | Roinestad et al. | |

* cited by examiner

Primary Examiner—F. L. Evans
(74) Attorney, Agent, or Firm—Jenkins Wilson & Taylor

(57) ABSTRACT

A sample measurement and analysis system comprises a fiber-optic channel selecting apparatus, a plurality of optical source lines, a plurality of optical return lines, a plurality of sample test sites, and an optical receiving device. The selecting apparatus comprises an optical input selection device, an optical output selection device, and a controller element. The optical input selection device defines a first optical path running between a first input end and a first output end. The first output end is rotatable to a plurality of first index positions defined along a first circular path. The optical output selection device defines a second optical path running between a second input end and a second output end. The second input end is rotatable to a plurality of second index positions defined along a second circular path. The controller element communicates with the optical input selection device and the optical output selection device for selectively aligning the first optical path with the first index positions and the second optical path with the second index positions.

37 Claims, 14 Drawing Sheets

SAMPLE ANALYSIS SYSTEM WITH FIBER OPTICS AND RELATED METHOD

FIELD OF THE INVENTION

The present invention relates generally to the coupling of selected input and output lines or channels through which optical signals are directed, and to the routing of optical signals to and from such lines or channels. More specifically, the present invention relates to an optical-based analysis system and method that utilizes a device adapted to effect selection and coupling through coordinated mechanical indexing movements and/or the use of optical fiber bundles whose ends are exposed to a detector. Such a device provides advantage in a wide variety of fields of application, particularly in applications involving the generation and transmission of analytical information. Specific fields of use include the preparation, sampling and analyzing of soluble materials as well as the testing of other fluids and solid materials exhibiting optical characteristics.

BACKGROUND OF THE INVENTION

Optical transport techniques are often utilized to direct a beam or pulse of light from a light source to a test site and, subsequently, to carry analytical information generated or measured at the test site to a suitable light receiving device. Analytical information transmitted by optical means can be chemical or biological in nature. For example, the analytical information can be used to identify a particular analyte, i.e., a component of interest, that is resident within the sample contained at the test site and to determine the concentration of the analyte. Examples of analytical signals include, among others, emission, absorption, scattering, refraction, and diffraction of electromagnetic radiation over differing ranges of spectra. Many of these analytical signals are measured through spectroscopic techniques. Spectroscopy generally involves irradiating a sample with some form of electromagnetic radiation (i.e., light), measuring an ensuing consequence of the irradiation (e.g., absorption, emission, or scattering), and interpreting of the measured parameters to provide the desired information. An example of an instrumental method of spectroscopy entails the operation of a spectrophotometer, in which a light source in combination with the irradiated sample serves as the analytical signal generator and the analytical signal is generated in the form of an attenuated light beam. The attenuated signal is received by a suitable input transducer such as a photocell. The transduced signal, such as electrical current, is then sent to a readout device.

As one example for implementing spectral analysis, a spectrophotometer uses ultraviolet (UV) and/or visible light, or in other cases infrared (IR) or near infrared (NIR) light, to scan the sample and calculate absorbance values. In one specific method involving the UV or UV-visible spectrophotometer, the UV sipper method, the sample is transferred to a sample cell contained within the spectrophotometer, is scanned while residing in the sample cell, and preferably is then returned to the test vessel.

The concentration of a given analyte in a sample through spectrochemical determination typically involves several steps. These steps can include (1) acquiring an initial sample; (2) performing sample preparation and/or treatment to produce the analytical sample; (3) using a sample introduction system to present the analytical sample to the sample holding portion of a selected analytical instrument (e.g., transferring the sample to the sample-holding portion of a UV spectrophotometer); (4) measuring an analytical signal (e.g., an optical signal) derived from the analytical sample; (5) establishing a calibration function through the use of standards and calculations; (6) interpreting the analytical signal based on sample and reference measurements; and (7) feeding the interpreted signal to a readout and/or recording system.

Conventional equipment employed in carrying out the above processes are generally known in various forms. Measurement of the analytical signal involves employing a suitable spectrochemical encoding system to encode the chemical information associated with the sample, such as concentration, in the form of an optical signal. In spectrochemical systems, the encoding process entails passing a beam of light through the sample under controlled conditions, in which case the desired chemical information is encoded as the magnitude of optical signals at particular wavelengths. Measurement and encoding can occur in or at sample cells, cuvettes, tanks, pipes, solid sample holders, or flow cells of various designs.

In addition, a suitable optical information selector is typically used to sort out or discriminate the desired optical signal from the several potentially interfering signals produced by the encoding process. For instance, a wavelength selector can be used to discriminate on the basis of wavelength, or optical frequency. A radiation transducer or photodetector is then activated to convert the optical signal into a corresponding electrical signal suitable for processing by the electronic circuitry normally integrated into the analytical equipment. A readout device provides human-readable numerical data, the values of which are proportional to the processed electrical signals.

For spectrophotometers operating according to UV-visible molecular absorption methods, the quantity measured from a sample is the magnitude of the radiant power or flux supplied from a radiation source that is absorbed by the analyte species of the sample. Ideally, a value for the absorbance A can be validly calculated from Beer's law:

$$A = -\log T = -\log\frac{P}{P_0} = abc,$$

where T is the transmittance, $P_0$ is the magnitude of the radiant power incident on the sample, P is the magnitude of the diminished (or attenuated) radiant power transmitted from the sample, a is the absorptivity, b is the pathlength of absorption, and c is the concentration of the absorbing species.

It thus can be seen that under suitable conditions, absorbance is directly proportional to analyte concentration through Beer's law. The concentration of the analyte can be determined from the absorbance value, which in turn is calculated from the ratio of measured radiation transmitted and measured radiation incident. In addition, a true absorbance value can be obtained by measuring a reference or blank media sample and taking the ratio of the radiant power transmitted through the analyte sample to that transmitted through the blank sample.

In some types of conventional sample testing systems, samples are transferred sequentially to one or more sample cells that are contained within the analytical instrument (e.g., spectrophotometer) itself. Samples are first taken from test vessels and, using sampling pumps, carried over sampling lines and through sampling filters. The samples are then transported to a UV analyzer, an HPLC system, a fraction collector, or the like. The analytical instrument may include a carousel that holds several sample cuvettes, such that rotation of the carousel brings each cuvette into position at the sample cell in a step-wise manner. The pulsing of the light source supplying the initial optical signal can be synchronized by control means with the rotation of the carousel.

Examples of UV-vis spectrophotometers are those available from Varian, Inc., Palo Alto, Calif., and designated as the CARY™ Series systems. In particular, the Varian CARY 50™ spectrophotometer includes a sample compartment that contains a sample cell through which a light beam or pulse passes. Several sizes of sample cells are available. In addition, the spectrophotometer can be equipped with a multi-cell holder that accommodates up to eighteen cells. A built-in movement mechanism moves the cells past the light beam.

Many conventional sample testing systems require either a plurality of active measurement beams, a plurality of active detectors, or both. For instance, U.S. Pat. No. 4,431,307 discloses a cuvette-set matrix containing an array of cuvettes adapted for use in measuring liquid samples using light beams. The cuvette-set matrix is adapted to receive a matrix of measurement beams such that one measurement beam is associated with each cuvette. A matrix of detectors is disposed on the side of the cuvettes opposite to the side at which the matrix of measurement beams is disposed. Thus, for each cuvette, the measurement beam emitted from the source passes through the liquid contained in the cuvette, and into the individual detector associated with that cuvette.

In other recently developed systems, fiber-optics are being used in conjunction with UV scans to conduct in-situ absorption measurements—that is, measurements taken directly in the sample containers of either dissolution test equipment or sample analysis equipment. Fiber optic cables consist of, for example, glass fibers coaxially surrounded by protective sheathing or cladding, and are capable of carrying monochromatic light signals.

One recent example of an in-situ fiber-optic method associated with dissolution testing is disclosed in U.S. Pat. No. 6,174,497. This method involves submerging a dip-type fiber-optic UV probe in test media contained in a vessel. Several probes can be operatively associated with a corresponding number of test vessels, with each probe communicating with its own UV spectrometer. A light beam (UV radiation) provided by a deuterium lamp is directed through fiber-optic cabling to the probe. Within the probe, the light travels through a quartz lens seated directly above a flow cell-type structure, the interior of which is filled with a quantity of the test media. The light passes through the test media in the flow cell, is reflected off a mirror positioned at the terminal end of the probe, passes back through the flow cell and the quartz lens, and travels through a second fiber-optic cable to a spectrometer.

Another recent example of an in-situ fiber-optic method associated with dissolution testing utilizes a U-shaped dip probe that is inserted into a test vessel. One leg of the U-shaped probe contains a source optical fiber and the other leg contains the return optical fiber. A gap between the ends of the fibers is defined at the base of the U-shape, across which the light beam is transmitted through the media of the test vessel.

For the previously described Varian CARY 50™ spectrophotometer, a fiber-optic dip probe coupler is available to enable in-situ sample measurement methods and effectively replace the need for a sipper accessory. This fiber optic coupler can be housed in the spectrophotometer unit in the place of the conventional sample cell. The coupler includes suitable connectors for coupling with the source and return optical fiber lines of a remote fiber-optic dip probe. The light beam from the light source of the spectrophotometer is directed to source line of the dip probe, and the resulting optical signal transmitted back to the spectrophotmeter through the return line.

Fiber optics have also been employed in connection with sample-holding cells. For example, U.S. Pat. No. 5,715,173 discloses an optical system for measuring transmitted light in which both a sample flow cell and a reference flow cell are used. Light supplied from a light source is transmitted through an optical fiber to the sample flow cell, and also through a second optical fiber to the reference flow cell. The path of transmitted light from each flow cell is directed through respective optical fibers toward an optical detector, and is controlled by an optical path switcher in the form of a light selecting shutter or disk.

It is acknowledged by persons skilled in the art that, when working with an array of flow cells, sample cells, cuvettes, probes, and other instruments of optical measurement, and particularly in connection with fiber-optic components, there remains a need for efficiently and effectively routing or distributing light energy to and from such sample containers. This need has been the subject of some developmental efforts.

For instance, U.S. Pat. No. 5,526,451 discloses a fiber-optic sample analyzing system in which a plurality of cuvettes each have a source optical fiber and a return optical fiber. A device is provided for selecting a source fiber to receive radiation for passage through a selected sample of one of the cuvettes, and for returning transmitted radiation from the selected cuvette through a selected return fiber to a spectrophotometer. The selection device includes a single rotatable retaining member supporting the respective ends of eight fiber-optic input lines and eight corresponding fiber-optic output lines. The respective ends of the fiber-optic lines are arranged in a ring around the central axis of the retaining member. The eight input lines define one half of the ring while the eight output lines define the other half. By this arrangement, each input line end affixed to the retaining member has a corresponding output line end affixed in diametrically opposite relation along the ring. Rotation of the retaining member determines which pair of input and output lines are respectively aligned with an input lens and an output lens disposed in spaced relation to the retaining member. A source beam passes through the input lens and into the selected input line at the end supported by the retaining member. The source beam then travels through the input line and into the sample cuvette associated with that particular input line. From the sample cuvette, the transmitted beam travels through the output line associated with the selected input line and sample cuvette. This output line terminates at its end supported by the retaining member. Since this output end is aligned with the output lens spaced from the retaining member, the transmitted beam passes through the output lens and is conducted to the analyzing means of the spectrophometer.

U.S. Pat. No. 5,112,134 discloses a vertical-beam photometric measurement system for performing enzyme-linked immunoabsorbent assay (ELISA) techniques. The system includes a light coupling and transmission mechanism utilizing a cylindrical rotor and a fiber-optic distributor. The mechanism receives light from a light assembly. The cylindrical rotor includes an optical fiber having an input end located at its center, and an output end located near its periphery. As the rotor rotates, the input end of the fiber of the rotor remains stationary with respect to the light assembly, while the output end moves around a circular path. The light output of the fiber of the rotor is received by a fiber optic distributor containing a multiplicity of optical fibers having their respective input ends arranged in a circular array. As the rotor is indexed about its axis, the output end of its fiber can be brought into alignment with successive fibers of the distributor. On the output side of the distributor, the multiplicity of fibers lead to a fiber manifold. The manifold aligns each fibers with a corresponding one of a multiplicity of assay sites. The assay sites are contained in a standard microplate consisting of an 8×12 array of optically transparent sample wells. Lens arrays are provided above and below the microplate to focus the beam of light passing through each individual sample well of the microplate. A detector board is located immediately below the lower lens array. The detector board contains an array of photodetectors corresponding to the array of sample wells. Thus, light from a selected fiber passes through a lens of the first lens array, the contents of the corresponding sample well, a corresponding lens of the second lens array, and into the corresponding photodetector of the detector board. In the conventional manner, the photodetector senses the intensity of the incident light that passed through the corresponding sample well and produces an electrical output signal proportional to the intensity. As in other vertical-beam systems adapted to scan samples contained in horizontally-oriented multi-well plates, this system requires a plurality of photedetectors and is not capable of routing the incident light from each sample well to a single detection means.

U.S. Pat. No. 6,151,111 also discloses a vertical-beam photometric system in which a plate carrier sequentially advances an 8×12 microplate through a measurement station. Each column of eight wells is scanned by light emitted from a bundle of eight corresponding distribution optical fibers. Light supplied from a light source passes through a monochromator to a rotor assembly. Each of the eight distribution fibers enables light from the rotor assembly to be sequentially directed by a corresponding mirror vertically through a corresponding aperture, lens, and microplate well, and subsequently into a corresponding photodetector lens. The rotor assembly consists of two mirrors positioned so as to bend light received by the rotor assembly 180 degrees, after which the light can be directed into one of the distribution fibers. The rotor can then be moved into alignment with another distribution fiber.

U.S. Pat. No. 4,989,932 discloses a multiplexer for enabling the sampling of a number of different samples. The multiplexer contains a stationary cylindrical outer body and a rotatable optical barrel disposed within the outer body. A primary inlet port is located on one side of the outer body through which light is introduced into the multiplexer. A primary exit port is located on an opposing side of the outer body through which light exits the multiplexer for transmission to an apparatus for optically analyzing a sample. Pairs of ancillary inlet and exit ports are disposed around the cylindrical wall of the outer body, and are oriented radially (or transversely) with respect to the longitudinal axis. The rotatable barrel contains a first mirror and lens associated with the ancillary exit ports, and a second mirror and lens associated with the ancillary inlet ports. A stepper motor is used to rotate the barrel to successively align the mirrors and lenses with a selected pair of ancillary inlet and exit ports. Light transmitted through the primary inlet port along the longitudinal axis of the multiplexer is turned at a right angle by the first mirror, passes through the first lens, and exits the multiplexer through the selected ancillary exit port. From the selected ancillary exit port, the light is transmitted through a fiber-optic bundle to a sample and returns to the multiplexer through the corresponding selected ancillary inlet port. From the selected ancillary inlet port, the light passes through the second lens, is turned at a right angle by the second mirror, and exits the multiplexer along the longitudinal axis. Other pairs of ancillary inlet and exit ports can be selected by rotating the barrel. In another embodiment disclosed in this patent, incoming light is received by an optical rod that has an angled mirrored surface at its end. Rotation of the rod by a stepper motor positions the angled mirrored surface to direct the light into a selected fiber-optic bundle.

U.S. Pat. No. 4,528,159 discloses a sample analysis system in which a belt containing a series of disposable reaction cuvettes is driven along a track so as to guide the cuvettes through several analysis stations. A separate photodetector tube is required for each analysis station. Light guides are used to transmit light from a light source, through filter wheels, through the reaction compartments of the cuvettes, and to the photodetectors.

U.S. Pat. No. 5,804,453 discloses a system in which a fiber-optic biosensor probe is inserted into a test tube. The probe receives a light beam from a light source and sends a testing signal to the photodetectors of a spectrometer. Time division multiplexing and demultiplexing is implemented to distribute light to and from several biosensors. Switching among inputs and outputs is controlled by an input control signal provided by an electronic clocked counter.

U.S. Pat. No. 5,580,784 discloses a system in which a plurality of chemical sensors are associated with several sample vials and arranged between a light source and a photodetector. Optical fibers are used to direct radiation into each sensor, as well as to direct emissions out from the sensors. A wavelength-tunable filter is combined with an optical multiplexer to direct radiation serially to each sensor through the fibers.

In view of the current state of the art, there is a continuing need for improved means for efficiently and effectively routing or distributing light energy to and from sample testing sites. It would be therefore be advantageous to provide a fiber-optic channel selection apparatus and method that utilize mechanical components to effect indexing among several optical input and/or output channels in an efficient and controlled manner without the need for costly optics-based switching components. In particular, it would be advantagous to provide an apparatus and method that enable analysis of multiple samples using only a single light source and a single detection means. Such an apparatus should be designed to minimize light loss and be compatible with a wide range of optical-based measurement systems. The present invention is provided to address these and other problems associated with the prior art.

SUMMARY OF THE INVENTION

According to one embodiment of the present invention, a sample measurement and analysis system comprises an optical channel selecting apparatus, a plurality of optical source lines, a plurality of optical return lines, a plurality of sample test sites, and an optical receiving device.

The optical channel selecting apparatus of the sample measurement and analysis system comprises an optical input selection device, an optical output selection device, and a controller element. The optical input selection device defines a first optical path running between a first input end and a first output end. The first output end is rotatable to a plurality of first index positions defined along a first circular path. The optical output selection device defines a second optical path running between a second input end and a second output end. The second input end is rotatable to a plurality of second index positions defined along a second circular path. The controller element communicates with the optical input selection device and the optical output selection device for selectively aligning the first optical path with the first index positions and the second optical path with the second index positions.

Preferably, the controller element comprises a rotatable coupling mechanism interconnecting the optical input selection device and the optical output selection device. Rotation of the coupling mechanism causes synchronized rotation of the first output end of the first optical path and the second input end of the second optical path.

In accordance with this embodiment, a light source can be optically coupled with the first input end of the first optical path. The plurality of optical source lines correspond to the plurality of first index positions and selectively communicate with the first optical path. The plurality of optical return lines correspond to the plurality of second index positions and selectively communicate with the second optical path. Each sample test site optically communicates with a corresponding one of the optical source lines and a corresponding one of the optical return lines. The optical signal receiving device optically communicates with the second output end of the second output path.

According to the invention, the sample test sites can take on various forms, depending on the particular function of purpose of the system in which the fiber-optic channel selecting apparatus is implemented. Non-limiting examples include sample containers, sample holders, sample cells, flow cells, optically transmissible multi-well plates, tanks, pipes, test vessels, cuvettes, test tubes, vials, and fiber-optic probes or dip probes. In one specific application of the invention, dip probes are insertable into test vessels containing the bulk media from which samples are taken or extracted. Insertion of the probes can be effected either manually or through automated means. The vessels can, for instance, contain dissolution media and be mounted on or otherwise supported by a dissolution test apparatus adapted to prepare the dissolution media. In other implementations, sample cells or flow cells are provided remotely in relation to the test vessels, and a suitable sample media transport system is provided for transferring samples to and from the cells and the vessels.

According to the invention, the optical signal receiving device can constitute any number of types of instruments, depending on the particular function of purpose of the system in which the fiber-optic channel selecting apparatus is implemented. In a specific exemplary embodiment of the invention, the optical signal receiving device is an optical detector such as a photodetector, phototube, photocell, or diode array.

According to another embodiment of the present invention, the fiber-optic channel selecting apparatus of the sample measurement and analysis system comprises an optical input selection device, an optical output selection device, and a rotatable coupling mechanism interconnecting the optical input selection device and the optical output selection device. The optical input selection device is rotatable about a first central axis, and comprises a first internal optical fiber having a first input end and a first output end. The first input end is disposed collinearly with the first central axis, and the first output end disposed at a radially offset distance from the first central axis. The optical output selection device is rotatable about a second central axis, and comprises a second internal optical fiber having a second input end and a second output end. The second input end is disposed at a radially offset distance from the second central axis, and the second output end disposed collinearly with the second central axis. Rotation of the coupling mechanism causes rotation of the first output end and the second input end.

In accordance with this embodiment, a light source can be optically coupled with the first input end of the first internal optical fiber. The plurality of optical source lines have respective source line input ends. Each source line input end is selectively optically alignable with the first output end of the first internal optical fiber. The plurality of optical return lines have respective return line output ends. Each return line output end is selectively optically alignable with the second input end of the second internal optical fiber. Each sample test site optically communicates with a corresponding one of the optical source lines and a corresponding one of the optical return lines. The optical signal receiving device optically communicates with the second output end.

According to an additional embodiment of the present invention, the sample measurement and analysis system comprises a fiber-optic channel selecting apparatus, a plurality of optical source lines, a mounting member, a plurality of optical return lines, a plurality of sample test sites, and an optical signal receiving device.

In this embodiment, the fiber-optic channel selecting apparatus comprising a rotary element rotatable about a central axis, and an internal optical fiber having an internal optical fiber input end and an internal optical fiber output end. The internal optical fiber input end is disposed collinearly with the central axis, and the internal optical fiber output end disposed at a radially offset distance from the central axis. A light source can be optically coupled with the first input end. The optical source lines have respective source line input ends. Each source line input end is selectively optically alignable with the internal optical fiber output end. The optical return lines have respective return line output ends. Each return line output end is fixedly supported by the mounting member. Each sample test site optically communicates with a corresponding one of the optical source lines and a corresponding one of the optical return lines. The optical signal receiving device is optically aligned with each return line output end.

According to a further embodiment of the present invention, a sample measurement and analysis system comprises an optical channel selection device, a plurality of optical source lines, a plurality of optical probes, and a plurality of optical return lines. The optical channel selection device defines an optical path running between an input end and an output end. The optical path is adjustable to a plurality of input channel positions. Each optical source line corresponds to a respective input channel position, and is selectively coupled to the optical path. Each probe is coupled to a respective source line. Each optical return line is coupled to a respective probe.

As described herein, the optical channel selecting apparatus of the inventive system can be provided as a mechanical, rotary fiber-optic multiplexer (and demultiplexer) apparatus for selecting channels through which a beam or pulse of light is routed in an indexing manner. The apparatus comprises one, two, or more rotary indexing devices. One of the rotary indexing devices demultiplexes a beam of light by distributing the light from a single, common outgoing or source line into a selected one of a plurality of outgoing or source channels. The selection is accomplished by rotating the demultiplexing device into a position at which the common outgoing or source line can optically communicate with the selected outgoing channel. The other rotary indexing device, when employed in the optical channel-selecting apparatus, multiplexes a beam of light for transmission into a single incoming or return line by selecting a selected one of a plurality of incoming or return channels. The selection is accomplished by rotating the multiplexing device into a position at which the common incoming or return line can optically communicate with the selected incoming or return channel. As an alternative to employing the multiplexing device, each incoming or return line can be optically aligned with a signal receiving means such as a photodetector, thereby eliminating the need for the second rotary indexing device and the common incoming or return line.

When two such rotary devices are provided in this manner, they can be mechanically interfaced so that rotation of one device concurs with rotation of the other device, with the result that the selection of a certain channel of the one device concurs with the selection of a corresponding channel of the other device. For instance, if each device includes twelve channels and thus twelve index positions, the selection of the channel at index position 1 of the one device simultaneously results in the selection of the channel at index position 1 of the other device.

According to an embodiment of the invention, each rotary device comprises two fixed components (i.e., first and second fixed components), a rotary component, and one or more bearings providing an interface between the fixed components and the rotary component. The rotary component is interposed between the two fixed components. Each fixed component faces a respective end of the rotary component. One of the fixed components (e.g., the first fixed component) has an optical aperture at its axial center. The other fixed component (e.g., the second fixed component) has a plurality of optical apertures oriented in a circular arrangement about its axial center. The number of optical apertures in the circular arrangement corresponds to the number of optical channels selectable by the apparatus of the invention. The rotary component has a light guiding path such as an optical fiber having one end located at the axial center of the rotary component and another end located radially outward with respect to the axial center. The centrally located end of the optical fiber of the rotary component is separated from the centrally located optical aperture of the first fixed component by a very small air gap. The offset end of the optical fiber of the rotary component is likewise separated from the plurality of optical apertures of the second fixed component by a very small air gap. These air gaps optimize light transmission while minimizing light loss, and avoid the necessity of using expensive additional optical components to couple the respective apertures and fiber ends of the fixed and rotary components. Indexed rotation of the rotary component with respect to the second fixed component results in selective coupling between the offset end of the optical fiber of the rotary component and each aperture of the second fixed component.

As indicated previously, the two rotary devices included with the optical channel selecting apparatus can be made to rotate together through a mechanical interface. This interface can be accomplished through a suitable set of gears arranged such that rotation of at least one gear results in rotation of both rotary devices. For example, each rotary device could be provided with its own gear, and each of these gears could be placed in meshing engagement with a third gear. While manual rotation of the third gear in order to rotate the other gears is possible, it is preferred that the third gear be powered through connection to a motor or similarly automated device. The motor could then be electronically controlled by suitable electronic hardware and/or software. As an alternative to providing gears with each rotary device, gear-like teeth could be formed on respective structures of the rotary devices to eliminate additional gearing. In either case, the rotary devices of the apparatus can be rotated continuously without the need to reverse rotation upon completion of the indexing of each channel provided. For instance, for a twelve-channel apparatus, the sampling interval from index position 1 to index position 2 is equivalent to the sampling interval from index position 12 to index position 1.

As an alternative, the first rotary device utilized to select an outgoing channel is provided, but the second rotary device utilized to select an incoming channel is eliminated in favor of suitably collecting a bundle of optical return fibers constituting the incoming channels at a fixed position at which the ends of the fibers are optically aligned with the receiving window of a optical detection device.

The invention as just described offers advantages when incorporated into any system that includes one or more light sources and one or more devices adapted for receiving light energy from the light sources. In such systems, the mechanical multiplexing/demultiplexing functions realized by the present invention are useful in networking one or more light signals from selected light sources to selected receiver devices. The invention also offers advantages when incorporated into any system that uses optics to route optical signals over several lines or channels between a single light source and a single detector. An example of this latter system is a UV-vis spectrophotometer, which is generally designed to conduct UV scans on prepared samples. It is often desirable to scan a multitude of samples. In accordance with the present invention, each sample can be held in a test vessel or a suitable cell or well, or in any other suitable sample holding or containment means, and fiber-optic input and output lines can be brought into operative communication with each sample test site, or with each probe associated with the sample test site. In this manner, each cell, probe, vessel or test site respectively becomes associated with one of the channels of the apparatus of the invention, and hence becomes associated with the corresponding index positions of the rotary device or devices of the apparatus. Accordingly, the selection of index position 1 of each rotary device, for example, corresponds to the selection of test vessel 1, cell 1, and so on.

The fiber-optic channel selecting apparatus according to any of embodiments described herein can be directly integrated into the design of an optical-based sample measurement and/or analysis system or instrument, such as a spectroscopic apparatus. An example of a spectroscopic apparatus is a spectrophotometer.

According to another aspect of the present invention, a method for acquiring data from samples comprises the following steps. A plurality of samples are respectively disposed at a plurality of test sites. A plurality of optical source lines are provided such that each source line communicates with a corresponding one of the plurality of test sites. A plurality of optical return lines are provided such that each return line communicates with a corresponding one of the test sites. A test site and its corresponding source line and return line are selected by rotating a fiber-optic channel selecting apparatus to a position at which a light source is coupled to the selected source line. An optical signal of a first intensity is sent through the selected source line to the selected test site to expose the sample that is disposed at the selected test site. An optical signal of a second intensity is emitted from the selected test site and travels through the selected return line. This process can be repeated for additional samples of the plurality of samples provided.

DETAILED DESCRIPTION OF THE INVENTION

In general, the term "communicate" (e.g., a first component "communicates with" or "is in communication with" a second component) is used herein to indicate a structural, functional, mechanical, optical, or fluidic relationship between two or more components or elements. As such, the fact that one component is said to communicate with a second component is not intended to exclude the possibility that additional components may be present between, and/or operatively associated or engaged with, the first and second components.

As used herein, the term "multiplexer" is broadly defined to indicate a system or device that includes a plurality of independent, individual input lines or channels and a single output line or channel (i.e., a common path or bus). One of the input lines can be selected so that its value or signal is transmitted or routed over the output line. Thus, the multiplexer could also be referred to as a data selector. In addition, the term "demultiplexer" is broadly defined herein as implementing the converse function of the multiplexer. That is, a demultiplexer is a system or device that includes one input line or channel (i.e., a common path or bus) and a plurality of output lines or channels. One of the output lines is selected to receive the value or signal provided by the input line. Thus, the demultiplexer could also be referred to as a data distributor. These terms, as used herein, are therefore intended to have a broader meaning than, for instance, the meanings typically understood by persons associated with the communications or electronics industries, wherein the terms are often restricted to meaning a system in which all elements of a given signal are observed simultaneously. For convenience, the term "multiplexer" or "multiplexing apparatus" as used hereinafter is intended to cover a device or system that includes a multiplexer and/or a demultiplexer.

As used herein, the terms "beam," "pulse," and "optical signal" are intended to be interchangeable to indicate that the present invention is applicable to the transmission of light energy by both continuous and non-continuous methods.

As used herein, the terms "aperture" and "bore" are used interchangeably to denote any opening through which light energy can be transmitted with an acceptable degree of efficiency and an acceptable minimum of light loss. Such an opening can include an optical fiber for these purposes as well. Whether the term "aperture" or "bore" is more appropriate could, for instance, depend on the thickness of the structural body through which the opening runs, but in any case the two terms are considered herein to be interchangeable.

Figure 1:
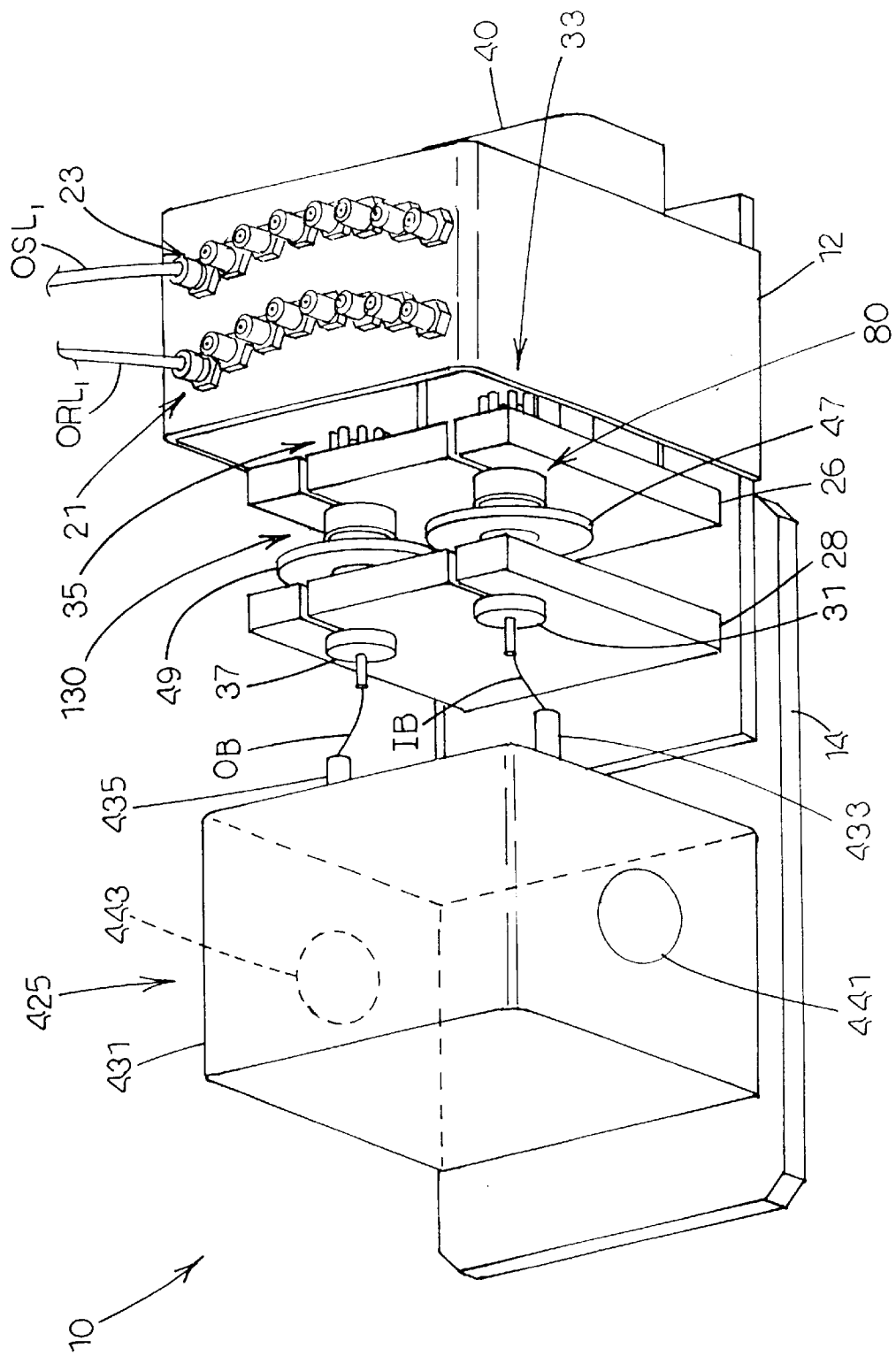
FIG. 1 is a perspective view of a fiber-optic channel selection apparatus provided in accordance with the present invention.
Figure 2:
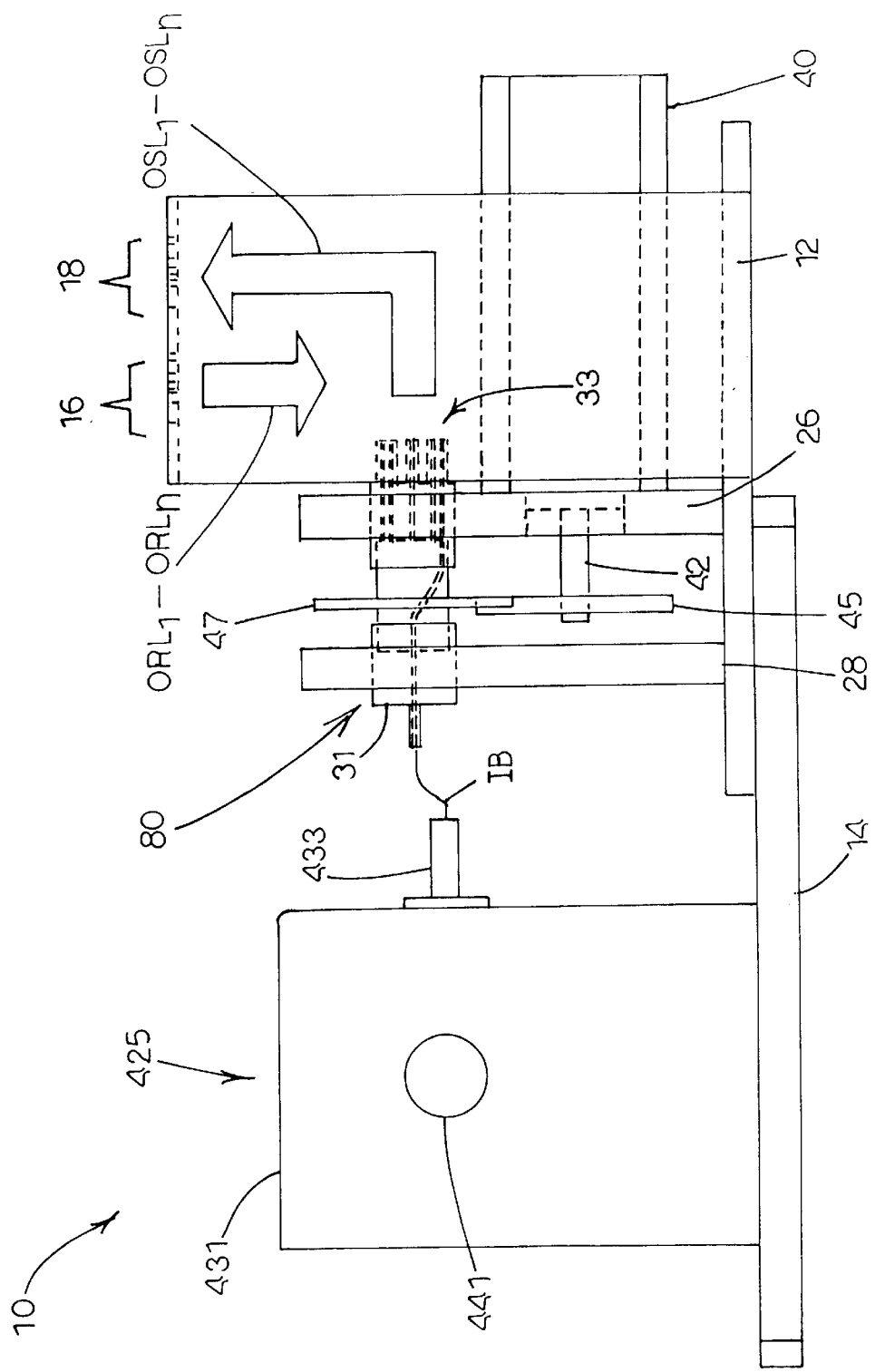
FIG. 2 is a side elevation view of the apparatus illustrated in FIG. 1.
Figure 3:
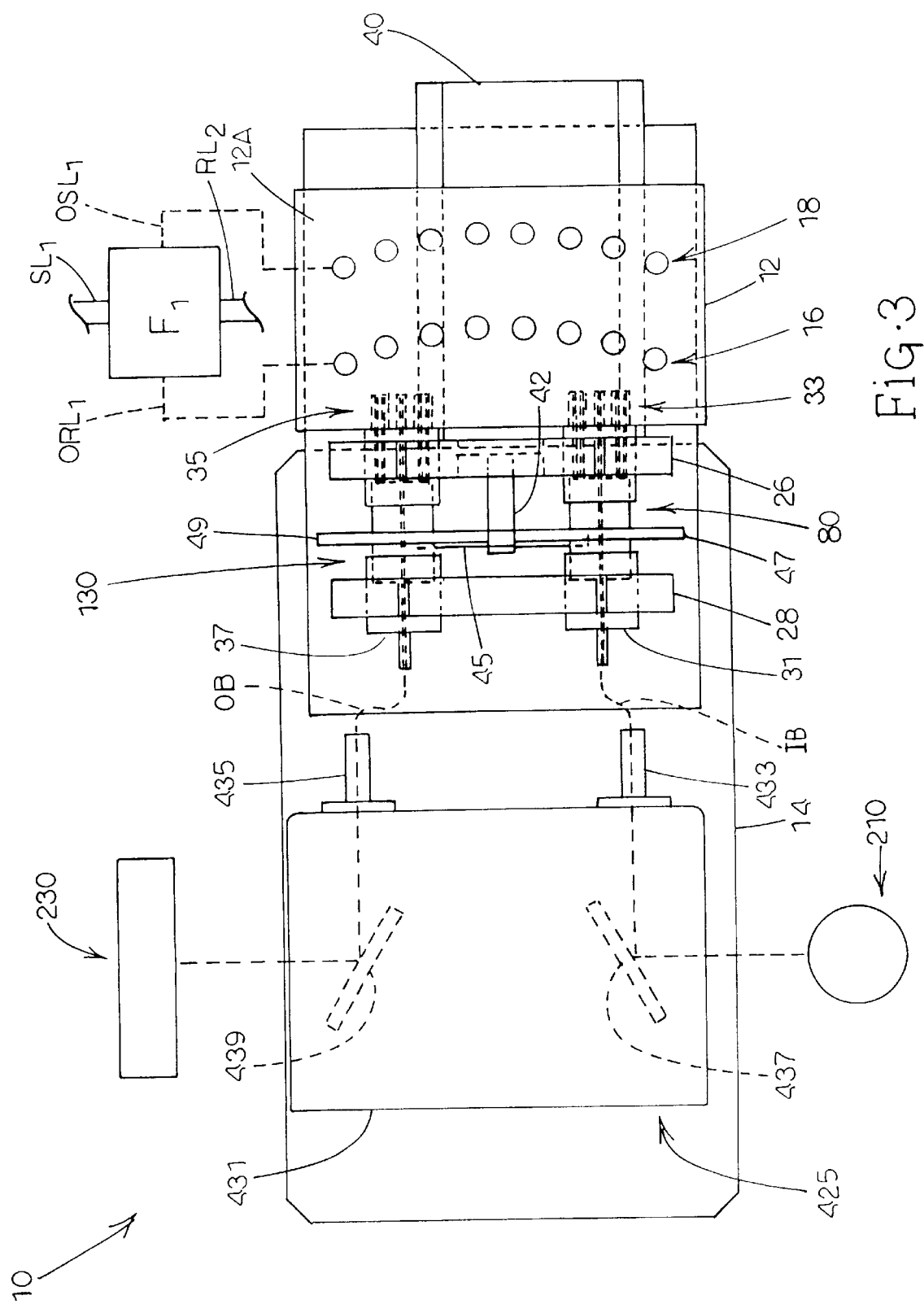
FIG. 3 is a top plan view of the apparatus illustrated in FIG. 1.

Referring now to FIGS. 1–4, an optical signal multiplexing apparatus, generally designated 10, is illustrated in accordance with the present invention. Multiplexing apparatus 10 comprises an enclosure 12 mounted to a base 14. Two rows of apertures (see FIG. 3), generally designated 16 and 18, respectively, are formed on a top surface 12A of enclosure 12. Two corresponding rows of fiber optic cable ferrules or fittings generally designated 21 and 23, respectively, (see FIG. 1) are mounted in these apertures 16 and 18. Individual fiber-optic source lines $OSL_1$–$OSL_n$ (where, in the illustrated exemplary embodiment, n=8) extend through the respective fittings of row 23 (and apertures 18), and individual fiber-optic return lines $ORL_1$–$ORL_n$ extend through the respective fittings of the other row 21 (and apertures 16). In FIGS. 1 and 3, only the first pair of optical source and return lines, optical source line $OSL_1$ and optical return line $ORL_1$, are shown. In FIG. 2, the respective bundles of optical source lines $OSL_1$–$OSL_n$ and optical return lines $ORL_1$–$ORL_n$ are schematically depicted by large arrows to indicate generally the direction of optical signals into and out from multiplexing apparatus 10.

Portions of enclosure 12 are removed in FIGS. 1–4 to illustrate the interior components disposed within enclosure 12. The primary operative interior components are two rotary indexing devices. One rotary device is referred to herein as an optical source line selector device, generally designated 80, and the other rotary device is referred to as an optical return line selector device, generally designated 130.

Source and return line selector devices 80 and 130 are situated adjacent to one another and are supported in fixed relation to each other, for example, by two axially spaced mounting blocks 26 and 28 that extend upwardly from base 14. A ferrule or input fitting 31 is connected to an input end of source line selector device 80. A circular array of fittings, generally designated 33, are connected to an output end of source line selector device 80. Another circular array of fittings, generally designated 35, are connected to an input end of return line selector device 130. A ferrule or output fitting 37 is connected to an output end of return line selector device 130. A common source line or input bus IB is connected to input fitting 31, and a common return line or output bus OB is connected to output fitting 37. As just described, each individual fiber-optic source line $OSL_1$–$OSL_n$ runs through a corresponding fitting 23 of aperture row 18, and each individual return line $ORL_1$–$ORL_n$ runs through fittings 21 mounted to aperture row 16. Although not specifically shown in FIG. 1 for clarity, each individual fiber optic source line $OSL_1$–$OSL_n$ is connected to a corresponding one of fittings 33 of source line selector device 80, and each individual return line $ORL_1$–$ORL_n$ is likewise connected to a corresponding one of fittings 35 of return line selector device 130. As described more fully below, source line selector device 80 functions to select which one of the fiber-optic source lines $OSL_1$–$OSL_n$ is optically coupled to input bus IB over a given interval of time. Return line selector device 130 functions to select which one of the fiber-optic return lines $ORL_1$–$ORL_n$ is optically coupled to output bus OB over the same interval of time.

Figure 4:
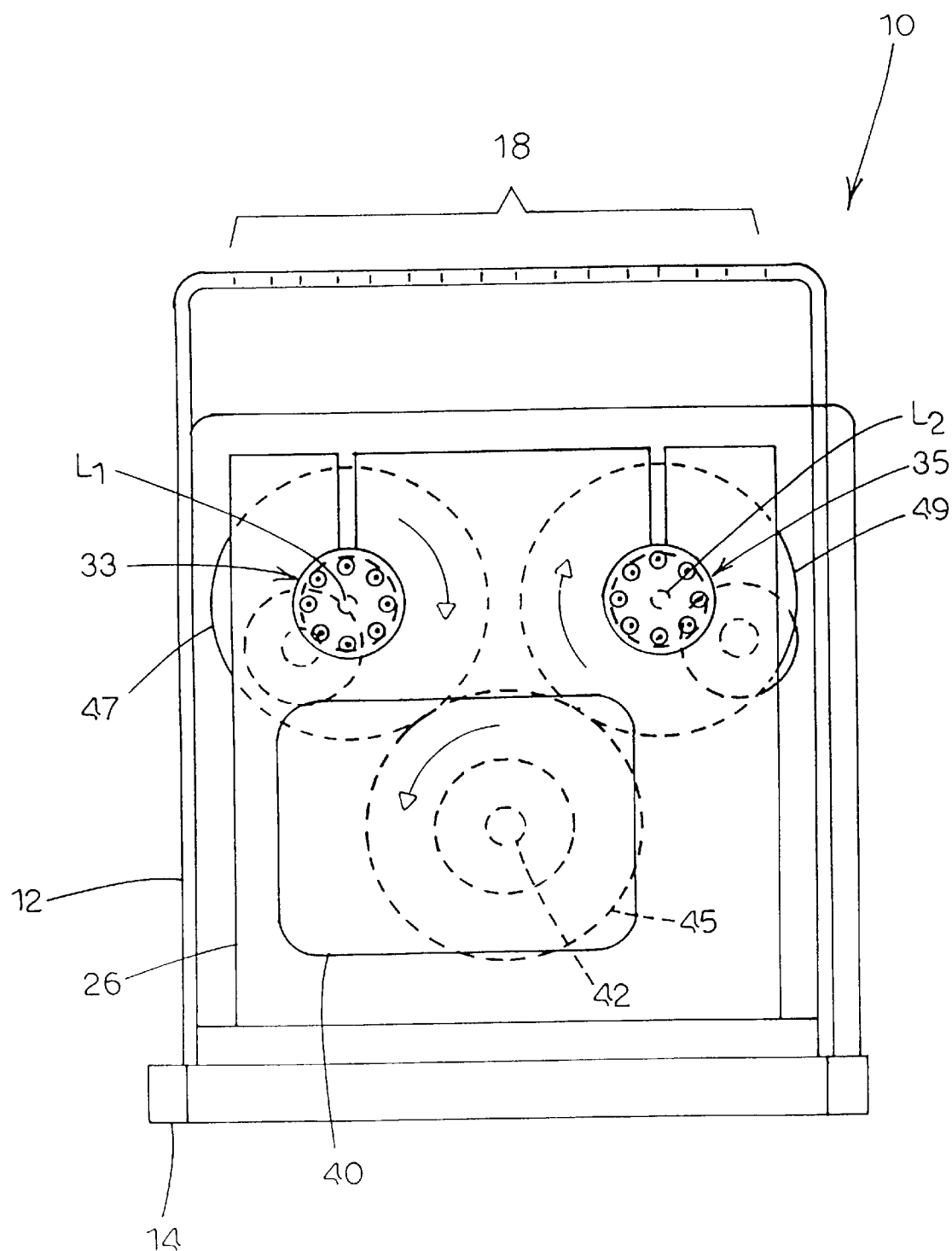
FIG. 4 is a rear elevation view of the apparatus illustrated in FIG. 1 showing the interconnection of rotary devices provided in accordance with one embodiment of the present invention.

As best shown in FIGS. 3 and 4, multiplexing apparatus 10 further comprises a means for causing both source line selector device 80 and return line selector device 130 to rotate simultaneously and in an indexing fashion. Preferably, the means is provided in the form of a powered mechanism adapted to transfer rotational force through a force transmission mechanism. In the exemplary embodiment illustrated in FIGS. 1–4, the powered mechanism is a motor 40 (such as, for example, a DC stepper motor) that causes a shaft 42 to rotate through programmed increments. The transmission mechanism includes an arrangement of gear wheels 45, 47 and 49. Gear wheel 45 is mounted to shaft 42 and thus rotates about the axis of shaft 42. Gear wheel 47 is mounted to source line selector device 80 and rotates about an axis $L_1$ of source line selector device 80 (see FIG. 4). Gear wheel 49 is mounted to return line selector device 130 and rotates about an axis $L_2$ of return line selector device 130. Gear wheels 47 and 49 are disposed in meshing engagement with gear wheel 45. Accordingly, clockwise rotation of gear wheel 45 results in counterclockwise rotation of both gear wheels 47 and 49. Conversely, counterclockwise rotation of gear wheel 45 results in clockwise rotation of both gear wheels 47 and 49. Moreover, gear wheels 47 and 49 are similarly sized and have the same number of teeth. As a result, rotation of gear wheel 45 through a given incremental arc length causes rotation of both gear wheels 47 and 49 through another proportional incremental arc length. The arc length through which gear wheel 47 rotates is the same as the arc length through which gear wheel 49 rotates.

As appreciated by persons skilled in the art, multiplexing apparatus 10 can be provided with means for verifying the positions of the various rotating components. For example, primary position verification can be effected by providing an optical encoder (not shown) that is focused on shaft 42 of motor 40. As a secondary mode of position verification, Hall effect sensors (not shown) can be provided to interface with a magnet (not shown) mounted on each gear wheel 47 and 49 respectively associated with source line selector device 80 and return line selector device 130. With respect to each source line selector device 80 and return line selector device 130, each corresponding set of Hall effect sensors would be mounted at each index position, such as by mounting the sensors in a circular array on a separate disks that rotates with corresponding barrel 85 or 135 in parallel with the magnet mounted to corresponding gear wheel 47 or 49.

Figure 5A:
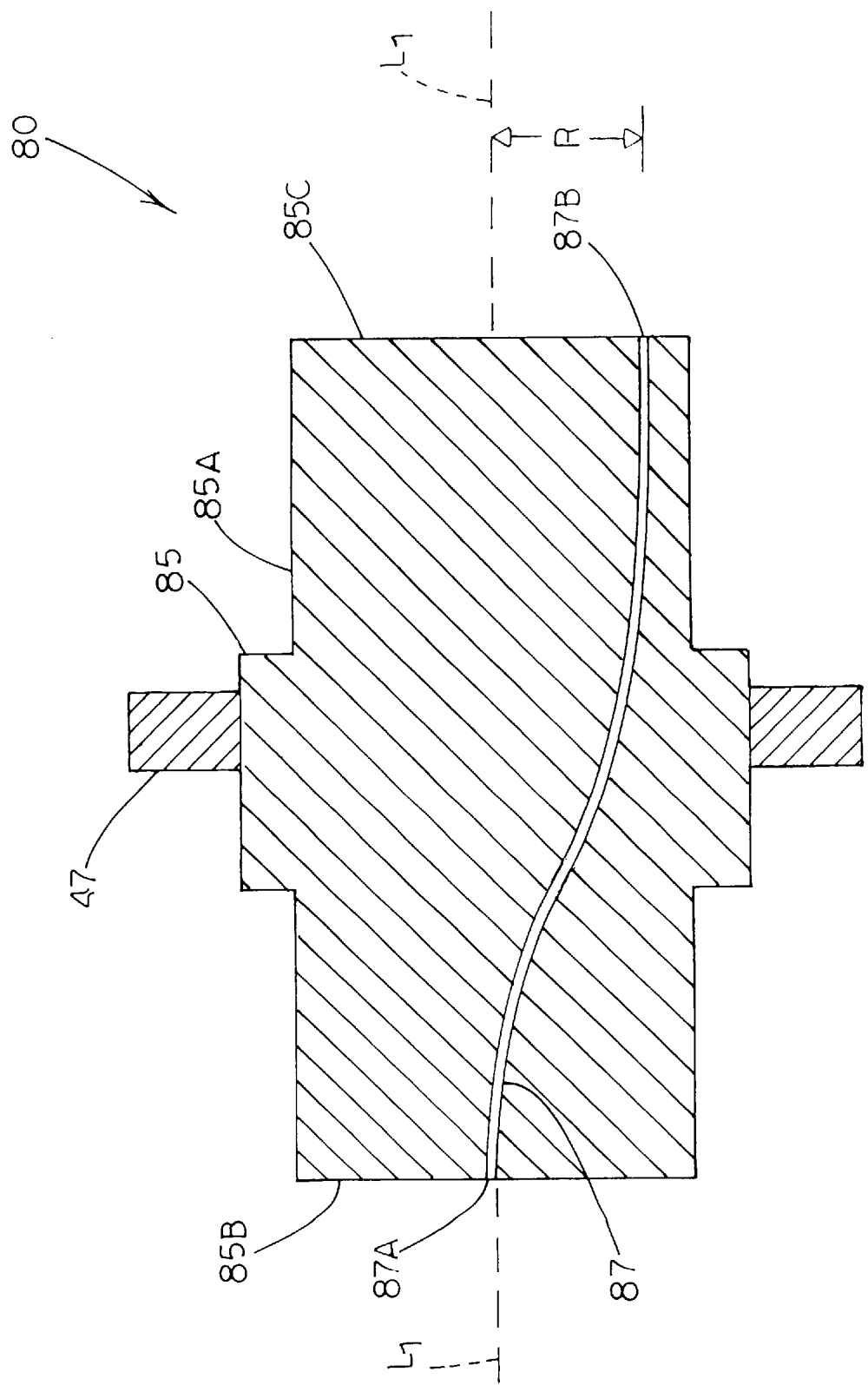
FIG. 5A is a cross-sectional view of a rotary device for distributing a light beam or signal from a single input to one or more fiber-optic channels in accordance with the present invention.

Referring now to FIGS. 5A–7C, details of source line selector device 80 and return line selector device 130 are illustrated. Referring specifically to FIG. 5A, source line selector device 80 comprises a rotary element or barrel 85 that is rotatable about its central axis $L_1$. Barrel 85 includes an outer lateral surface 85A, an input end surface 85B, and an output end surface 85C. Gear wheel 47 is fitted around the periphery of outer lateral surface 85A. Gear wheel 47 is either a separate component or comprises teeth formed around barrel 85. An internal bore 87 extends through the body of barrel 85, and has an input bore end 87A opening at input end surface 85B and an output bore end 87B opening at output end surface 85C. Input bore end 87A is coincident with axis $L_1$, and thus the position of input bore end 87A in relation to axis $L_1$ does not change during rotation of barrel 85. Output bore end 87B, on the other hand, is disposed at a location on output end surface 85C that is offset from axis $L_1$ by a radial offset distance equal to radius R. Rotation of barrel 85 about axis $L_1$ therefore results in rotation of output bore end 87B along a circular path of radius R, as defined on output end surface 85C with respect to axis $L_1$. An internal optical fiber 90 (see FIG. 6A) extends throughout internal bore 87. Internal optical fiber 90 terminates at an input fiber end 90A (see FIG. 6A) located at input bore end 87A, and terminates at an output fiber end 90B (see FIG. 6A) located at output bore end 87B. Thus, input fiber end 90A is coincident with axis $L_1$ and output fiber end 90B is offset from axis $L_1$ by radial offset distance (or radius) R. Rotation of barrel 85 about axis $L_1$ does not affect the position of input fiber end 90A, but results in a circumferential change in the position of output fiber end 90B with respect to axis $L_1$.

Figure 6A:
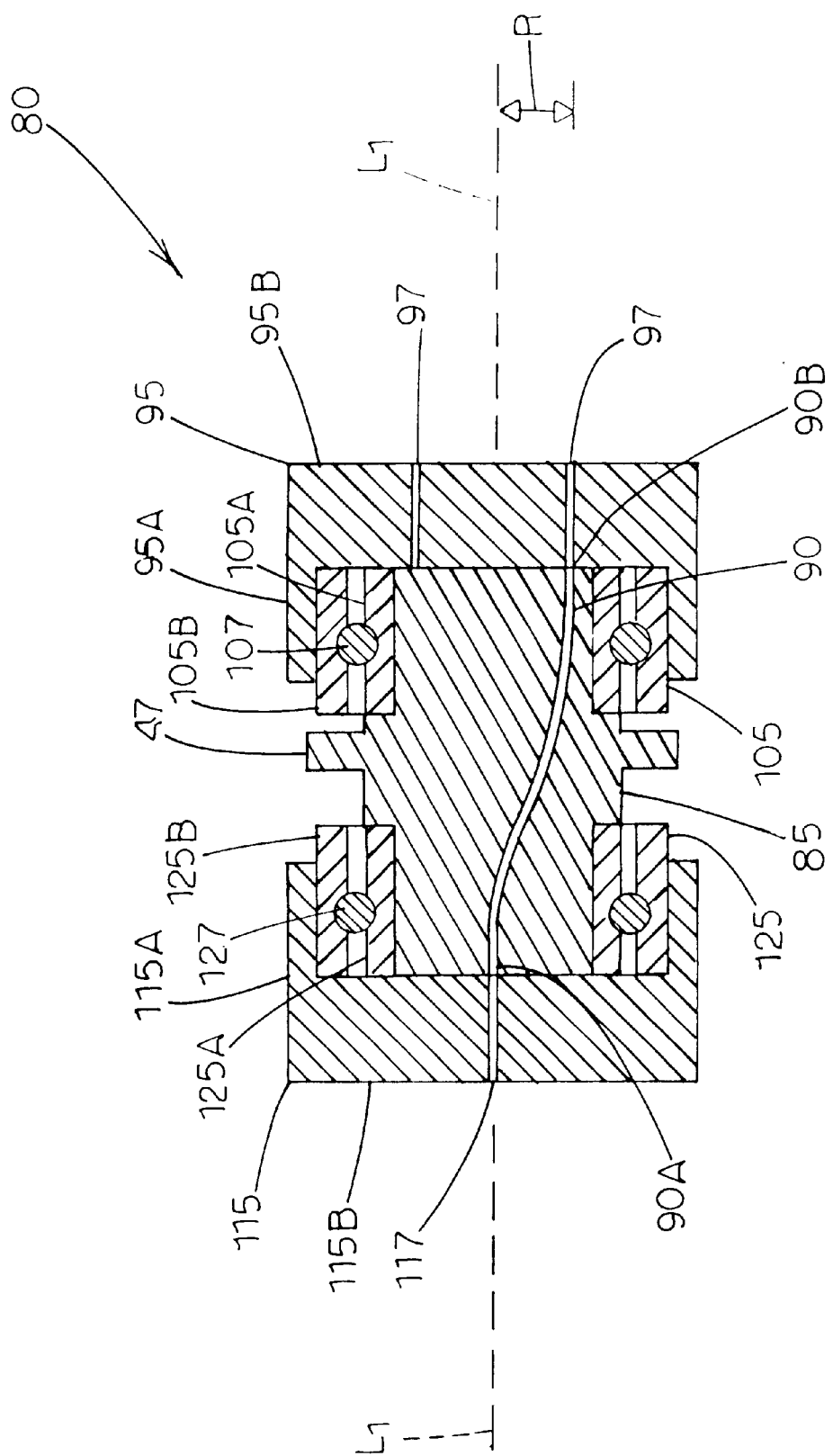
FIG. 6A is a cross-sectional view of an optical input selection device provided with the apparatus illustrated in FIGS. 1–4, including the rotary device illustrated in FIG. 5A.

Referring to FIG. 6A, source line selector device 80 is designed to permit rotational indexing of barrel 85 about axis $L_1$. Through this rotational movement, output fiber end 90B can be selectively positioned at one of a plurality of equally spaced index locations around a circumference on output end surface 85C. This circumference is swept out by the conceptual end point of radius R in relation to axis $L_1$. In order to implement source fiber "channel" or line selection, barrel 85 rotates with respect to some type of stationary member that includes a number of fixed-position optical reception points corresponding to the plurality of index locations. In FIG. 6A, for example, the channel selection is implemented according to the invention by providing a stationary optical reception member. In the present embodiment, the stationary optical reception member is a bearing sleeve or cap 95 disposed at the output side of barrel 85. A bearing 105 provides an interface between rotatable barrel 85 and stationary bearing sleeve 95. As illustrated in FIG. 6A, bearing 105 can be a roller bearing of conventional design that includes an inner ring 105A, an outer ring 105B, and a series of balls 107 contacting the respective, opposing raceways of inner ring 105A and outer ring 105B. As understood by persons skilled in the art, balls 107 typically are interposed between inner ring 105A and outer ring 105B and in a circumferentially spaced arrangement through the use of a retaining element (not shown) forming some type of frame, cage, or carriage around each ball 107. Inner ring 105A firmly contacts (such as by press fitting) lateral outer surface 85A of barrel 85, while outer ring 105B firmly contacts at least the inner surface of an annular section 95A of bearing sleeve 95. By this arrangement, inner ring 105A rotates with barrel 85 while outer ring 105B remains in a fixed position with stationary bearing sleeve 95. It will be understood that bearing 105 could be either a ball bearing or a needle bearing, or some other type of bearing that permits barrel 85 to rotate in a stable manner with respect to bearing sleeve 95. That is, rotatable needle elements could be substituted for balls 107 illustrated in FIG. 6A.

In addition to its annular section 95A, bearing sleeve 95 includes a plate section 95B transversely oriented with respect to axis $L_1$ of source line selector device 80. Plate section 95B is immediately adjacent to output end surface 85C of barrel 85. Plate section 95B includes a plurality of apertures 97 (only two of which are shown in FIG. 6A) arranged in a circular array of radius R with respect to axis $L_1$. These apertures 97 constitute the previously described fixed-position optical reception points. The actual number of apertures 97 corresponds to the number of indices at which output fiber end 90B of internal optical fiber 90 can be selectively positioned, and accordingly corresponds to the number of individual optical channels or lines into which an optical signal traveling through internal optical fiber 90 from input fiber end 90A can be selectively directed through output fiber end 90B. The specific number of apertures 97 (and hence the specific number of individual optical channels and index positions) will depend on the number of test sites to which optical source signals are to be sent. Besides the test sites that contain analytical samples, one or more of these test sites could hold reference or control samples (e.g., sources for obtaining blank or standard measurement data). In the example shown in FIG. 7B, plate section 95B of bearing sleeve 95 includes an array of eight apertures 97 to handle eight separate optical channels or lines. It will be understood, however, that more or less apertures 97 could be provided, again depending on the number of separate optical channels.

The specific provision of bearing 105 and bearing sleeve 95, in the arrangement and design illustrated in FIG. 6A, ensures that any light loss from the light conducting components of source line selector device 80 is negligible. The size of the air gap between output end surface 85C of barrel 85 and plate section 95B of bearing sleeve 95 is preset to provide optimal light transmission. Annular section 95A and plate section 95B of bearing sleeve 95 cooperatively form a shoulder around bearing 105 and output end surface 85C to prevent light losses. In furtherance of the purpose of preventing light loss in this particular arrangement, it is preferable that the axial edges of inner ring 105A and outer ring 105B of bearing 105 facing plate section 95B of bearing sleeve 95 be substantially flush with output end surface 85C of barrel 85.

Although source line selector device 80 and its barrel 85 are not expected to encounter axial thrust forces during the operation of multiplexing device 10, source line selector device 80 can further include a second bearing 125 and corresponding bearing sleeve 115 mounted at the input side, as also shown in FIG. 6A. The design and arrangement of input-side bearing 125 and bearing sleeve 115 can be similar to those of output-side bearing 105 and bearing sleeve 95. Input-side bearing sleeve 115 thus includes an annular section 115A and a plate section 115B. As one principal difference, however, input-side bearing sleeve 115 includes only one aperture 117 formed in its plate section 115B (see also FIG. 7A). This single aperture 117 is situated coincident with axis $L_1$ and is immediately adjacent to input fiber end 90A of internal optical fiber 90. The inclusion of input-side bearing 125 and bearing sleeve 115 lends stability to the indexing movements of barrel 85 and overall operation of source line selector device 80, and further facilitates the optical coupling of internal optical fiber 90 to input bus IB (see FIG. 1). Input-side bearing 125 can comprise balls 127 interposed between an inner ring 125A and an outer ring 125B.

Figure 5B:
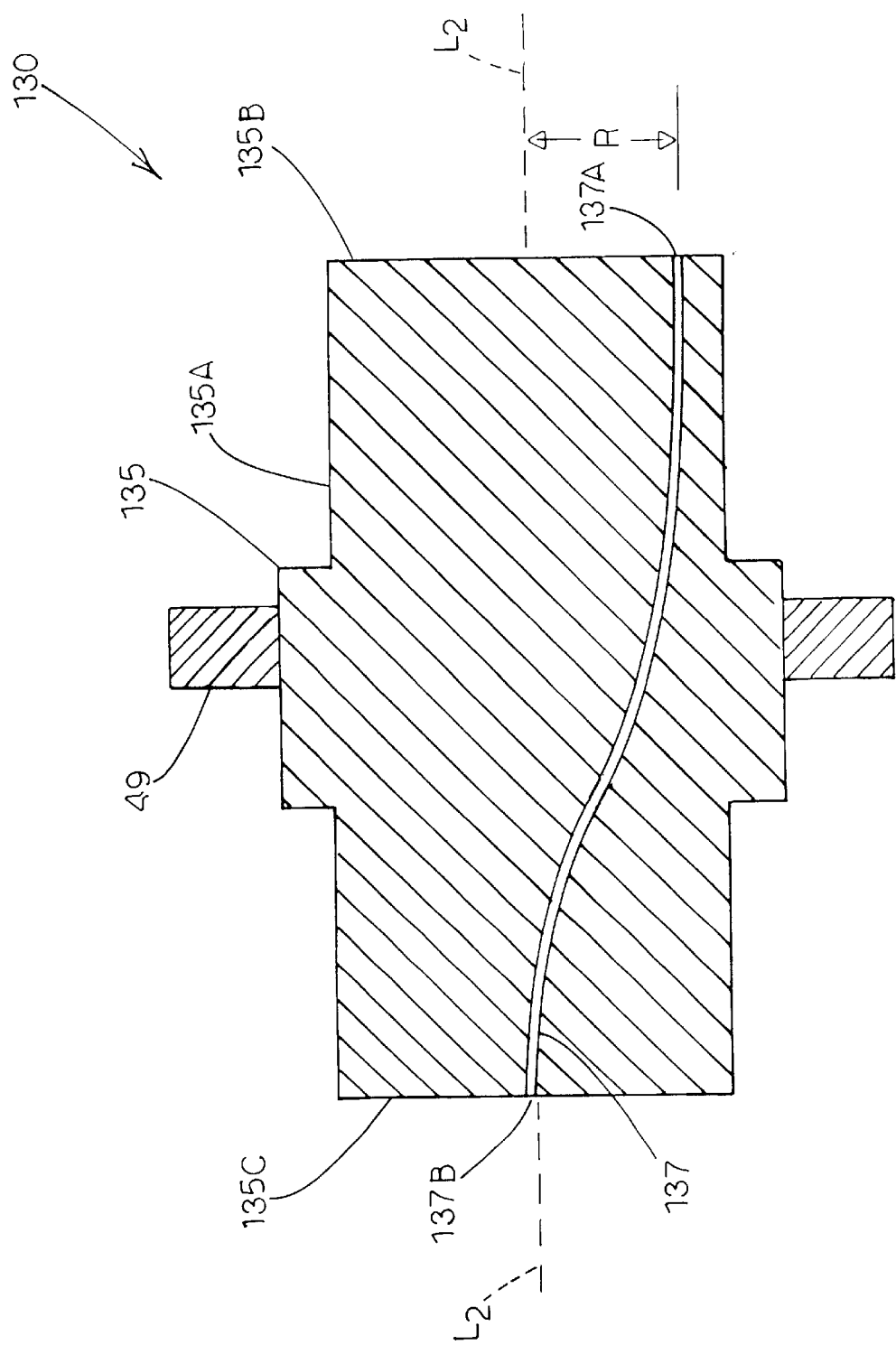
FIG. 5B is a cross-sectional view of a rotary device for distributing light beams or signals from one or more fiber-optic channels to a single output in accordance with the present invention.

Referring to FIG. 5B, return line selector device 130 comprises features similar to those of source line selector device 80 although, as shown in FIG. 1, the axial positions of the input and output sides of return line selector device 130 are reversed in comparison to those of source line selector device 80. Specifically, return line selector device 130 comprises a rotary element or barrel 135 rotatable about its central axis $L_2$. Barrel 135 includes an outer lateral surface 135A, an input end surface 135B, and an output end surface 135C. Gear wheel 49 is fitted around the periphery of outer lateral surface 135A. Gear wheel 49 is either a separate component or comprises teeth formed around barrel 135. An internal bore 137 extends through the body of barrel 135, and has an input bore end 137A opening at input end surface 135B and an output bore end 137B opening at output end surface 135C. Input bore end 137A is disposed at a location on input end surface 135B that is offset from axis $L_2$ by a radial offset distance equal to radius R. Rotation of barrel 135 about axis $L_2$ therefore results in rotation of input bore end 137A along a circular path of radius R defined on input end surface 135B with respect to axis $L_2$. Output bore end 137B, on the other hand, is coincident with axis $L_2$ such that its position in relation to axis $L_2$ does not change during rotation of barrel 135. An internal optical fiber 140 extends throughout internal bore 137. Internal optical fiber 140 (see FIG. 6B) terminates at an input fiber end 140A located at input bore end 137A, and terminates at an output fiber end 140B located at output bore end 137B. Thus, input fiber end 140A is offset from axis $L_2$ by radial offset distance (or radius) R and output fiber end 140B is coincident with axis $L_2$. Rotation of barrel 135 about axis $L_2$ does not affect the position of output fiber end 140B, but results in a circumferential change in the position of input fiber end 140A with respect to axis $L_2$.

Figure 6B:
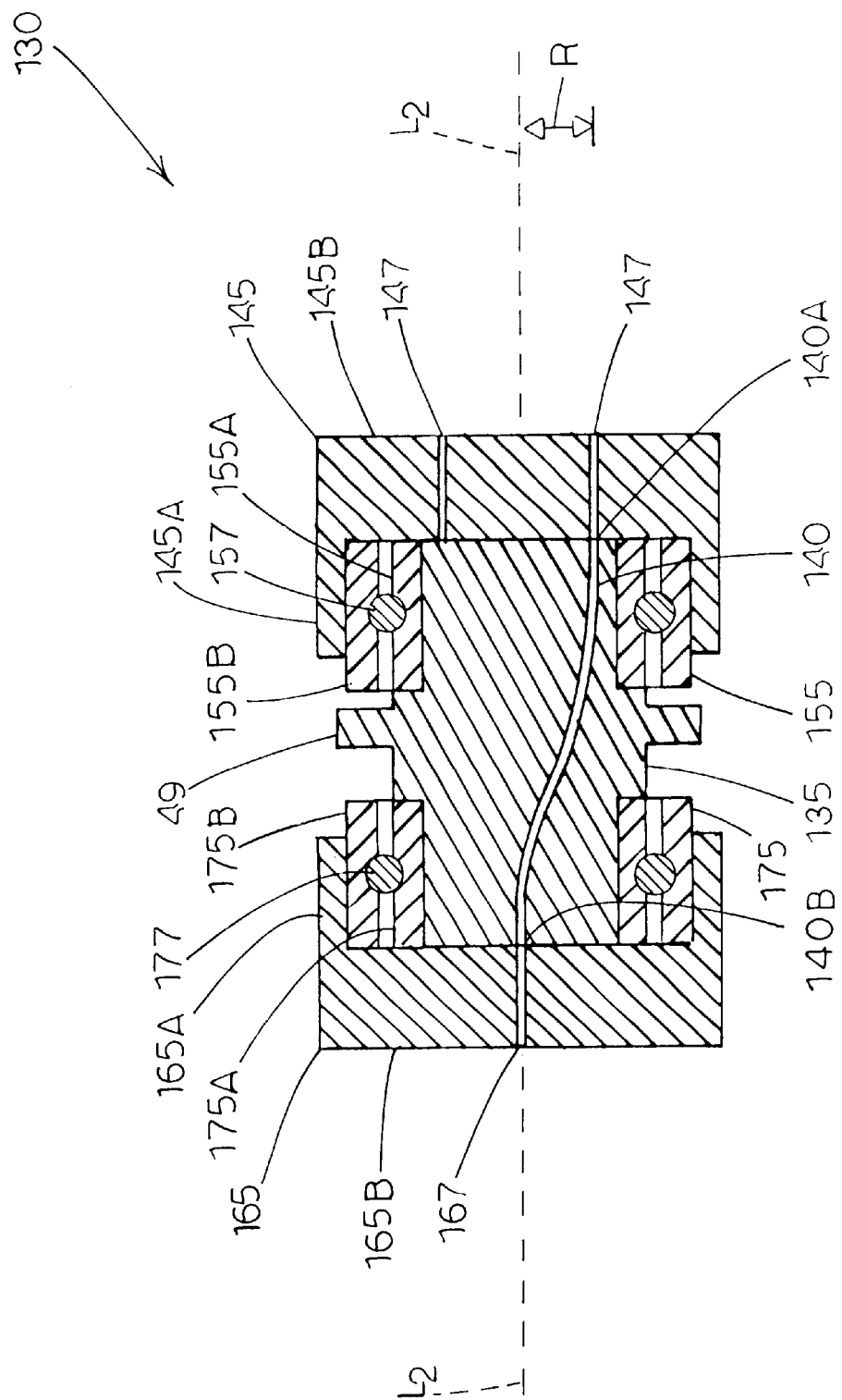
FIG. 6B is cross-sectional view of an optical output selection device provided with the apparatus illustrated in FIGS. 1–4, including the rotary device illustrated in FIG. 5B.

Referring to FIG. 6B, return line selector device 130 enables rotational indexing of barrel 135 about axis $L_2$ in a manner analogous to source line selector device 80. Through the rotational movement effected by return line selector device 130, its input fiber end 140A can be selectively positioned at one of a plurality of equally spaced index locations around a circumference of radius R defined on input end surface 135B. In order to implement return fiber "channel" or line selection, return line selector device 130 includes a stationary bearing sleeve 145 disposed at the output side of barrel 135. As in the case of source fiber selector device 80, barrel 135 rotates with respect to bearing sleeve 145. A bearing 155 provides an interface between rotatable barrel 135 and stationary bearing sleeve 145. Bearing 155 can be provided in the form of a roller bearing that includes an inner ring 155A, an outer ring 155B, and a series of balls 157 or needles according to conventional designs. Inner ring 155A rotates with barrel 135 while outer ring 155B remains in a fixed position with stationary bearing sleeve 145.

Bearing sleeve 145 of return line selector device 130 comprises an annular section 145A coaxially disposed around bearing 155 and a plate section 145B transversely oriented with respect to axis $L_2$ of return line selector device 130. Plate section 145B is immediately adjacent to input end surface 135B of barrel 135 with an air gap therebetween, which is dimensioned for optimal optical transmission. Annular section 145A and plate section 145B of bearing sleeve 145 cooperatively form a shoulder around bearing 155 and input end surface 135B. This arrangement of bearing 155 and bearing sleeve 145 ensures that any light loss from the light conducting components of return line selector device 130 is negligible. In furtherance of the purpose of preventing light loss in this particular arrangement, it is preferable that the axial edges of inner ring 155A and outer ring 155B of bearing 155 facing plate section 145B of bearing sleeve 145 be substantially flush with input end surface 135B of barrel 135.

Plate section 145B includes a plurality of apertures 147 (only two of which are shown in FIG. 6B) arranged in a circular array of radius R with respect to axis $L_2$. These apertures 147 constitute fixed-position optical coupling points between the individual return fibers $ORL_1$–$ORL_n$ and input fiber end 140A of internal optical fiber 140. The actual number of apertures 147 corresponds to the number of indices at which input fiber end 140A can be selectively positioned, and accordingly corresponds to the number of individual optical channels or lines from which an optical signal can be selectively directed into input fiber end 140A. The specific number of apertures 147 (and hence the specific number of individual optical channels and index positions) will depend on the number of sites or detection areas from which optical return signals are to be received.

As also shown in FIG. 6B, return line selector device 130 can further include a second bearing 175 and corresponding bearing sleeve 165 mounted at the output side. The design and arrangement of output-side bearing 175 and bearing sleeve 165 can be similar to those of input-side bearing 105 and bearing sleeve 95. Output-side bearing sleeve 165 thus includes an annular section 165A and a plate section 165B. Output-side bearing sleeve 165, however, includes only one aperture 167 formed in its plate section 165B. This single aperture 167 is situated coincident with axis $L_2$ and is immediately adjacent to output fiber end 140B of internal optical fiber 140 and, on the other side, to output bus OB (see FIG. 1). Output-side bearing 175 can comprise balls 177 interposed between an inner ring 175A and an outer ring 175B.

Figure 7C:
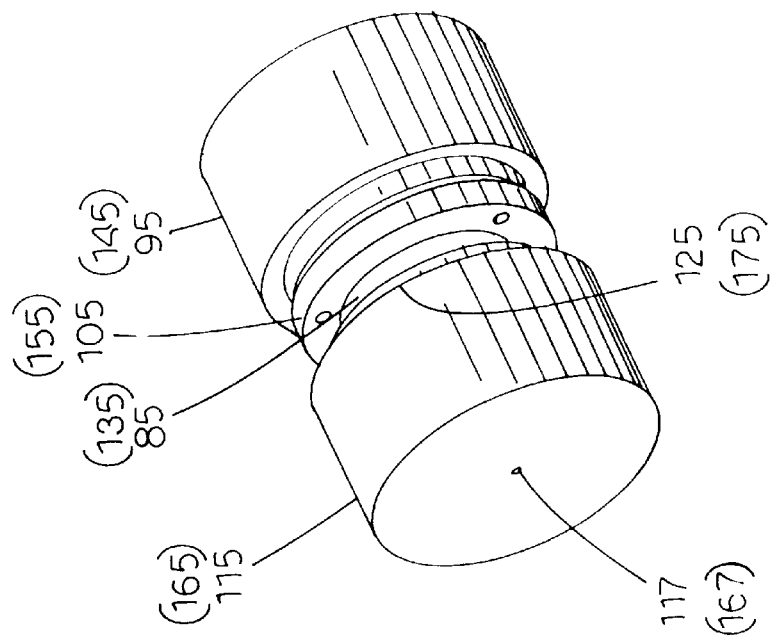
FIG. 7C is a perspective view of either of the optical input selection device illustrated in FIG. 6A or the optical output selection device illustrated in FIG. 6B.
Figure 7B:
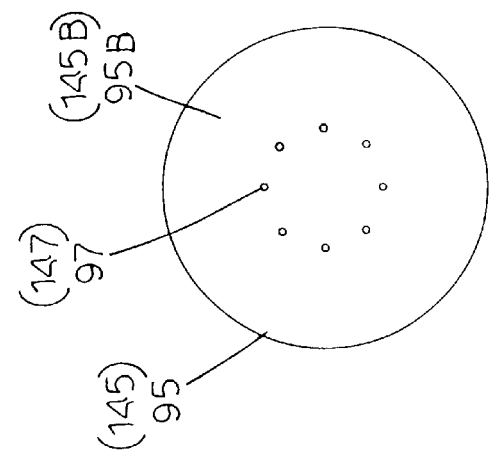
FIG. 7B is a plan view illustrating either the output side of the optical input selection device illustrated in FIG. 6A or the input side of the optical output selection device illustrated in FIG. 6B.
Figure 7A:
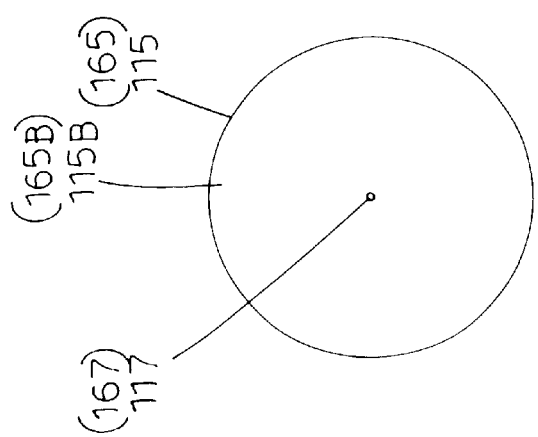
FIG. 7A is a plan view illustrating either the input side of the optical input selection device illustrated in FIG. 6A or the output side of the optical output selection device illustrated in FIG. 6B.

FIG. 7A illustrates plate section 115B and single aperture 117 of input-side bearing sleeve 115 of source line selector device 80. FIG. 7B illustrates plate section 95B and multiple apertures 97 of output-side bearing sleeve 95 of source line selector device 80. FIG. 7C illustrates input-side bearing sleeve 115, output-side bearing sleeve 95, and bearings 105 and 125 assembled onto barrel 85 of source line selector device 80. It will be understood that FIGS. 7A–7C are likewise representative of the structure of return line selector device 130, but with the input and output sides reversed. That is, FIG. 7A could represent plate section 165B and single aperture 167 of output-side bearing sleeve 165 of return line selector device 130, and FIG. 7B could represent plate section 145B and multiple apertures 147 of input-side bearing sleeve 145 of return line selector device 130. Likewise, FIG. 7C can be considered as illustrating input-side bearing sleeve 145, output-side bearing sleeve 165, and bearings 155 and 175 assembled onto barrel 135 of return line selector device 130.

Figure 8:
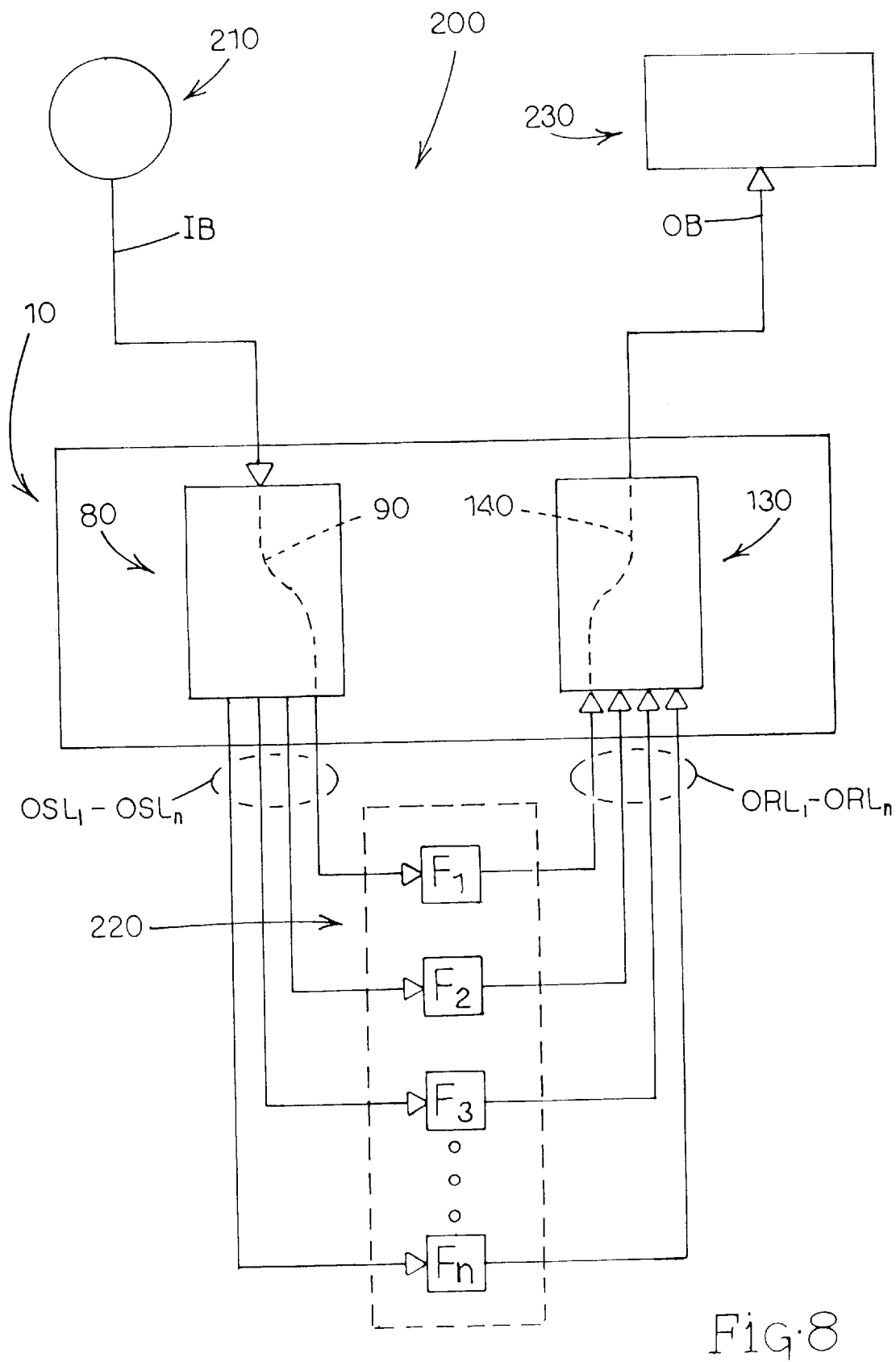
FIG. 8 is a schematic diagram of an analytical testing and data acquisition system in which the apparatus or portions thereof illustrated in FIGS. 1–7C is incorporated in accordance with the present invention.

According to another aspect of the invention, FIG. 8 illustrates the general features of an analytical testing and data acquisition system, generally designated 200, in which multiplexer apparatus 10 can advantageously operate. In addition to multiplexer apparatus 10, analytical testing system 200 comprises a light source, generally designated 210, a data encoding or analytical signal generating system or arrangement, generally designated 220, and an optical signal receiving device or system generally designated 230.

Light source 210 can be any type of suitable continuous or non-continuous optical source. Non-limiting examples include deuterium arc lamps, xenon arc lamps, quartz halogen filament lamps, and tungsten filament lamps. In one specific example, a pulsed light source such as a xenon flash lamp could be employed to emit very short, intense bursts of light. This type of lamp flashes only when acquiring a data point, as compared to a diode array that exposes the sample to the entire wavelength range with each reading and potentially causes degradation of photosensitive samples. As described in commonly assigned U.S. Pat. No. 6,002,477, because it emits light on a non-continuous basis, the xenon flash lamp does not require a mechanical means such as a chopper for interrupting the light beam during measurement of a dark signal. One specific example of a xenon flash lamp that is capable of acquiring eighty data points per second is employed in CARY™ Series spectrophotometers commercially available from Varian, Inc, Palo Alto, Calif.

Data encoding or analytical signal generating system 220 can comprise any device or system adapted to contain and expose one or more samples to the light energy supplied by light source in order to encode information about that sample as the light passes through the sample and the sample is irradiated. For example, data encoding system could constitute an array of test sites $F_1$–$F_n$ such as sample measurement and/or holding sites. These test sites $F_1$–$F_n$ can be defined by a variety of sample measurement/containment components, such as solid sample holders, sample containers or cells, test vessels, flow cells, tanks, pipes, the wells of a quartz microtitre plate or similar microcells capable of transmitting light, and specially designed fiber-optic probes.

Signal receiving device or system 230 could be any type of instrument or system of instruments adapted to receive and process the optical signals supplied by data encoding device 220. The specific property of the sample substance to be analyzed will dictate the type of equipment or instrumentation used to analyze samples taken from, for example, test vessels $V_1$–$V_8$ shown in FIG. 10. Moreover, the various components comprising signal receiving device 230 will depend on the type of analytical signal to be measured and detected. If the desired analytical signal is the intensity of light radiation absorbed by analytes at each test site $F_1$–$F_n$, absorbance values can be calculated in order to determine the concentration of the target substance (i.e., the analyte of interest). For this purpose, signal receiving device 230 in FIG. 8 can comprise a UV-vis spectrophotometer. The invention, however, is not limited to any specific design of spectrophotometer. Possible configurations for the spectrophotometer include those that utilize single detectors or multi-channel detectors, those that are adapted to perform single-beam or double-beam measurements, those that are adapted to perform horizontal-beam or vertical-beam measurements, and those that can perform measurements of fixed wavelength or of the entire absorption spectra for the sample. Moreover, for the purpose of the present disclosure, the terms "signal receiving device or system" and "sample analyzing system" are intended to encompass any analyzing equipment compatible with the systems and methods described herein. Such equipment may include, but is not limited to, HPLC, spectrometers, photometers, spectrophotometers, spectrographs, and similar equipment. In the case of a spectrophotometer, signal receiving device 230 typically includes light source 210, a wavelength selector or similar device, a radiation detector such as a photoelectric detector or transducer, a signal processor, and a readout device.

Referring to the schematic depiction of analytical testing and data acquisition system 200 illustrated in FIG. 8, light source 210 optically communicates with source line selector device 80 of multiplexing apparatus 10 via input bus IB, and optical signal receiving device 230 optically communicates with return line selector device 130 via output bus OB. In the present embodiment, data encoding system 220 comprises a set of sample measurement components or test sites $F_1$–$F_n$ (e.g., flow cells, sample cells, test vessels, or the like), each of which is adapted to contain or provide a target for a sample to be analyzed. Source line selector device 80 optically communicates with sample measurement components $F_1$–$F_n$ via the set of optical source lines $OSL_1$–$OSL_n$, respectively, and return line selector device, 130 optically communicates with sample measurement components $F_1$–$F_n$ via a set of optical return lines $ORL_1$–$ORL_n$, respectively. For clarity, only four each of optical source lines $OSL_1$–$OSL_n$, sample measurement components $F_1$–$F_n$, and optical return lines $ORL_1$–$ORL_n$ are shown in FIG. 8. By this arrangement, each sample measurement component $F_1$–$F_n$ can receive an incident light input of an initial intensity $P_0$ from light source over a corresponding optical source line $OSL_1$–$OSL_n$, and subsequently transmit a light output of an intensity P to optical signal receiving device for processing and readout over a corresponding optical return line $OSL_1$–$OSL_n$. As described previously, respective internal optical fibers 90 and 140 of source and return line selector devices 80 and 130 are rotatably indexed in mutual synchronization. As a result, the selection of optical source line $OSL_1$, for example, to carry the source signal from internal optical fiber 90 of source line selector device 80 to sample measurement component $F_1$ concurs with the selection of optical return line $ORL_1$ to carry the attenuated signal transmitted from sample measurement component $F_1$ to internal optical fiber 140 of return line selector device 130.

Referring back to FIG. 3, some of the features of the system described with reference to FIG. 8 are schematically shown in operative communication with multiplexing apparatus 10. Light source 210 optically communicates with input bus IB, and output bus OB optically communicates with signal receiving device 230. Sample measurement component $F_1$ optically communicates with optical source line $OSL_1$ and optical return line $ORL_1$. In addition, sample measurement component $F_1$ is illustrated in the form of a liquid phase-containing sample holding cell, and accordingly is illustrated as fluidly communicating with a media sample line $SL_1$ and a media return line $RL_1$. As described hereinabove, optical source line $OSL_1$ is connected to one of fittings 33 of source line selector device 80, and optical return line $ORL_1$ is connected to one of fittings 35 of return line selector device 130. It will be understood that other sample measurement components $F_2$–$F_n$ can be analogously interfaced with multiplexing apparatus 10 and other corresponding media sample lines and media return lines (not shown).

The operation of sample analysis system 200 with sample cells (e.g., sample cell or flow cell $F_1$ as shown in FIG. 3) will now be described. One or more samples of media are transferred from selected test vessels (which could be, for example, mounted in a dissolution test apparatus or other appropriate media preparation/testing apparatus) through media sample lines (e.g., sample line $SL_1$ in FIG. 3) to corresponding sample cells $F_1$–$F_n$. After optical measurements are taken, the samples can be, if the system is so configured, returned to the test vessels through media return lines (e.g., return line $RL_1$ in FIG. 3). Calibration operations can also be carried out prior to test runs as needed.

Multiplexing apparatus 10 is operated as described with reference to FIGS. 1–7C. Preferably, the movements of multiplexing apparatus 10 are coordinated with the operations of the other elements of sample analysis system 200 under the control of a suitable electronic processing device such as a computer (not shown). Accordingly, source line and return line selector devices 80 and 130 of multiplexing apparatus 10 are initially set to their respective home positions. At the home positions, one of the bundle of optical fiber source lines $OSL_1$–$OSL_n$ is positioned (e.g., at "index position 1") in optical coupling relation with optical input bus IB, and a corresponding one of the bundle of optical fiber return lines $ORL_1$–$ORL_n$ is positioned (e.g., at a corresponding "index position 1") in optical coupling relation with optical output bus OB. In effect, multiplexing apparatus 10 selects the sample measurement component $F_1$–$F_n$ corresponding to the selected index position of source and return selector devices 80 and 130.

To take a measurement of the sample residing in the selected sample measurement component, light source 210 sends a beam of light of intensity $P_0$ into input bus IB. Source line selector device 80 is positioned such that the light is routed into the selected one of the bundle of source lines $OSL_1$–$OSL_n$. This source beam (or pulse) is thus transmitted into the particular sample measurement component $F_1$–$F_n$ that corresponds to the selected source line $OSL_1$–$OSL_n$ and return line $ORL_1$–$ORL_n$. Light source 210 and the sample residing in the selected sample measurement component can together be considered as a signal generator, in that light source 210 and the sample conjoin to generate the analytical signal in the form of an attenuated beam of light of intensity P as the beam of light passes through the sample. The analytical signal is transmitted through the selected one of return lines $ORL_1$–$ORL_n$ back to multiplexing apparatus 10 and, due to the position of return line selector device 130, is routed into output bus OB. Output bus OB transmits the analytical signal to signal receiving device 230 for detection and processing, and the concentration of the measured sample is determined from the value obtained from its measured light absorbance, using calibration curves if necessary.

Within signal receiving device 230, a wavelength selector is typically provided in the form of a filter or monochromator that isolates a restricted region of the electromagnetic spectrum for subsequent processing. The detector converts the radiant energy of the analytical signal into an electrical signal suitable for use by the signal processor. The signal processor can be adapted to modify the transduced signal in a variety of ways as necessary for the operation of signal receiving device 230 and the conversion to a readout signal. Functions performed by the signal processor can include amplification (i.e., multiplication of the signal by a constant greater than unity), logarithmic amplification, ratioing, attenuation (i.e., multiplication of the signal by a constant smaller than unity), integration, differentiation, addition, subtraction, exponential increase, conversion to AC, rectification to DC, comparison of the transduced signal with one from a standard source, and/or transformation of the electrical signal from a current to a voltage (or the converse of this operation). Finally, a readout device displays the transduced and processed signal, and can be a moving-coil meter, a strip-chart recorder, a digital display unit such as a digital voltmeter or CRT terminal, a printer, or a similarly related device.

As indicated previously, remote flow cells are but one type of means for encoding information that can be processed by signal receiving device 230. Other examples of sample measurement components are fiber-optic probes, or dip probes, that are designed for insertion directly into a container holding an analyte-containing media. In some applications, the use of dip probes has been a substitute for the removal (and preferably the subsequent return) of samples from the media container and the transfer of the samples to the sample cell of a spectroscopic or other sample analyzing apparatus.

Figure 9:
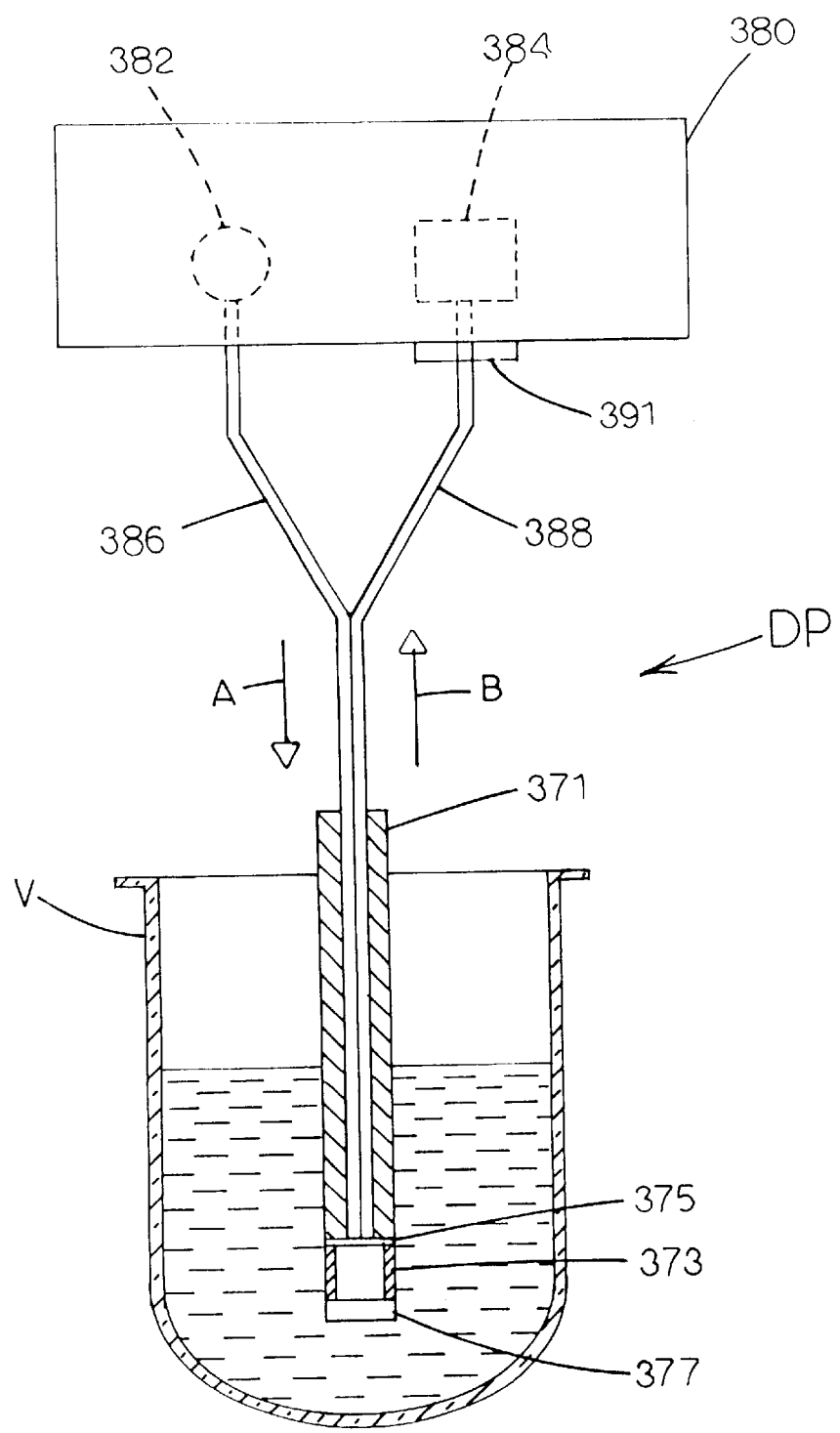
FIG. 9 is a schematic diagram of a fiber-optic probe operating in conjunction with a test vessel and a spectrophotometer according to conventional methods.

Referring now to FIG. 9, an example of a dip probe of conventional design, generally designated DP, is illustrated. In typical use, dip probe DP is inserted into a test vessel V so that the lower portion of its tip 371 is submerged in media held by test vessel V, thereby allowing absorbance measurements to be taken directly in test vessel V. Dip probe DP typically includes a detection area or cavity 373 similar to a flow cell that is defined by a gap between a fused silica or quartz lens or seal 375 and a mirror 377. Dip probe DP is illustrated operating in conjunction with a spectrophotometer 380 that includes a light source 382 and a photodiode amplifier/detector 384. A first, light-transmitting fiber-optic cable 386 runs between spectrophotometer 380 and glass seal 375. A second, light-returning fiber-optic cable 388 runs between glass seal 375 back to spectrophotometer 380, and usually includes an interference filter 391 or similar component. In use, a beam of light emitted by light source 382 is guided by first fiber-optic cable 386 along the direction of arrow A into detection area 373. This beam of light passes through the media residing in detection area 373, is reflected by mirror 377, and thus is redirected into second fiber-optic cable 388 along the direction indicated by arrow B. The light beam then passes through interference filter 391 and returns to spectrophotometer 380 where the signal is processed by detector 384. Preferably, the length of detection area 373 is half the optical pathlength, as the light passes through the solution twice before reaching detector 384.

Figure 10:
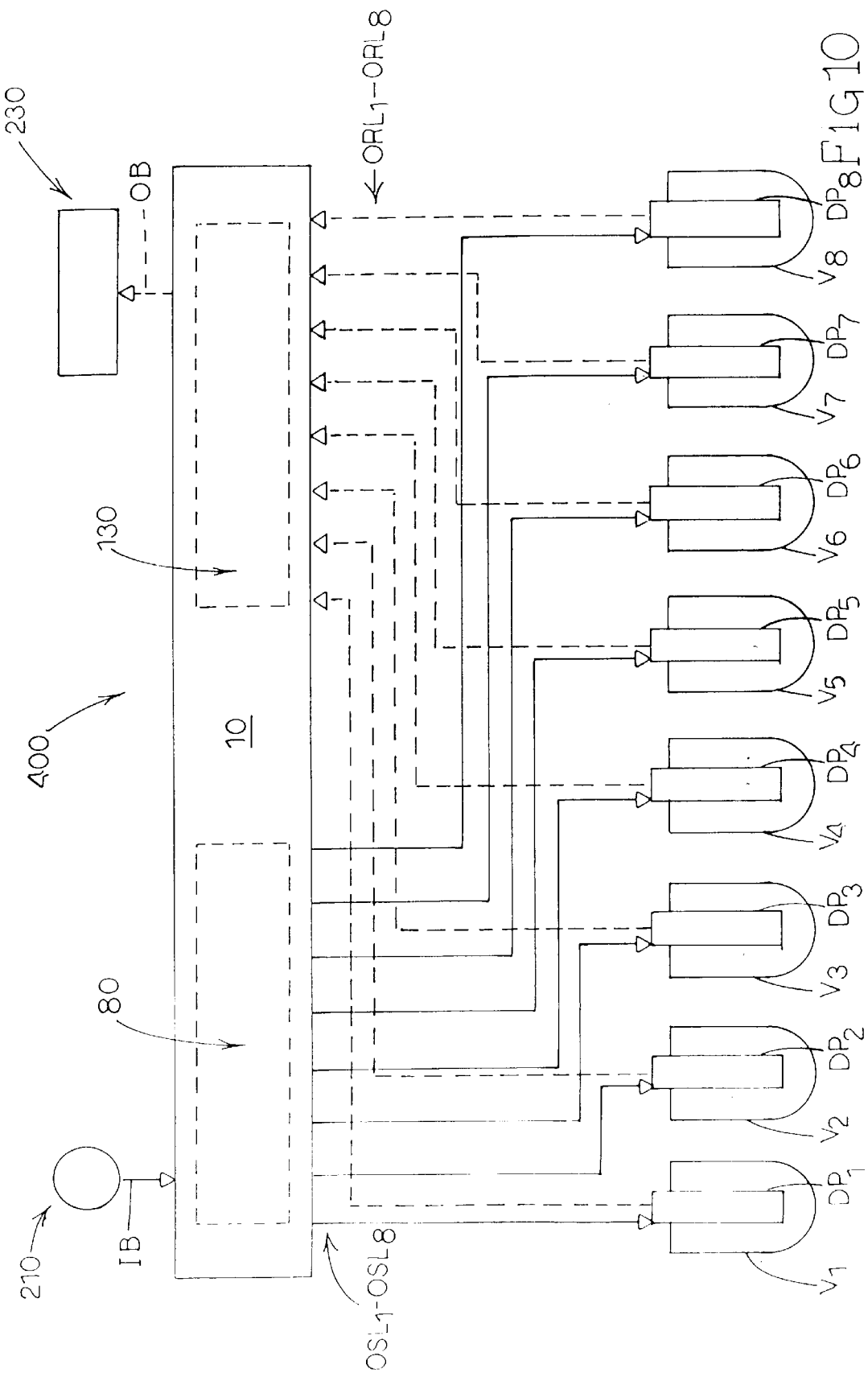
FIG. 10 is a schematic diagram of an in-situ measurement system incorporating the use of the apparatus or portions thereof illustrated in FIGS. 1–7C in combination with fiber-optic probes or similar instruments.

Referring now to FIG. 10, an in-situ measurement system, generally designated 400, is illustrated as a specific application of analytical testing and data acquisition system 200 described hereinabove with reference to FIGS. 3 and 8. In-situ measurement system 400 comprises multiplexer apparatus 10, light source 210, and optical signal receiving device or system 230. In this particular embodiment of the invention, in-situ measurement system 400 further provides a data encoding device or analytical generating system in the form of an array of dip probes $DP_1$–$DP_8$ or similar instruments that are insertable into corresponding test vessels $V_1$–$V_8$. Hence, sample measurements are taken directly in test vessels $V_1$–$V_8$. One or more of vessels $V_1$–$V_8$, however, can serve as blank and/or standard media vessels. Each dip probe $DP_1$–$DP_8$ is connected to a corresponding pair of optical source lines $OSL_1$–$OSL_8$ (indicated by solid lines) and return lines $ORL_1$–$ORL_8$ (indicated by dashed lines). Source and return line selector devices 80 and 130 of multiplexing apparatus 10 function in the manner described hereinabove to selectively couple each source line $OSL_1$–$OSL_8$ with input bus IB and each corresponding return line $ORL_1$–$ORL_8$ with output bus OB. As in previously described embodiments, light source 210 communicates with input bus IB and signal receiving device 230 communicates with output bus OB. As one alternative, each dip probe $DP_1$–$DP_8$ could be mounted to the automated sampling assembly of a media preparation/testing apparatus 300, such that each dip probe $DP_1$–$DP_8$ could be inserted into its vessel $V_1$–$V_8$ to take a measurement and thereafter removed according to a programmed, automated schedule.

In addition to the use of sample containment means such as flow cells, dip probes and the like as specified hereinabove, other means and accessories can be employed for generating analytical data in accordance with the invention. For example, instead of absorption probes, reflectance probes can be employed for undertaking reflectance measurements of samples. As appreciated by persons skilled in the art, a typical reflectance probe includes two fiber-optic bundles. One bundle forms a central core and delivers light to the sample. The other bundle surrounds the central core, and collects the light reflected from the sample and returns it to the detector of the associated sample analyzing instrument. Alternatively, a transmission probe can be employed to enable the measurement of solid samples. A typical transmission probe includes two single optical fibers. One fiber delivers light to the sample, and the other collects the light transmitted through the sample and returns the transmitted light to the sample analyzing instrument. The transmission probe is preferably used in conjunction with a sample holder adapted to position the sample for measurement. The nature of the sample (e.g., textile fabrics, sunglasses) dictates the design of the sample holder. Transmittance data can also be acquired from solid samples using an integrating sphere, which is a hollow sphere having an internal surface that is a non-selective diffuse reflector. Integrating spheres are often used to measure the transmission of turbid, translucent, or opaque refractory materials in situations where other techniques are inadequate due to loss of light resulting from the scattering effects of the sample.

Referring back to FIGS. 1–3, while input bus IB can be directly coupled to light source 210 and output bus OB directly coupled to signal receiving device 230, this is not a requirement of the invention. The invention contemplates that various accessories and adaptations can be employed, such as those indicated hereinabove, and that multiplexing apparatus 10 can be integrated with existing analytical systems, in accordance with specific applications of multiplexing apparatus 10. For example, in FIGS. 1–3, multiplexing apparatus 10 can additionally include a fiber-optic coupling unit, generally designated 425, for routing light beams into and out from fiber-optic cables. Fiber-optic coupling unit 425 comprises an enclosure 431, fittings 433 and 435 mounted to one or more walls of enclosure 431, one or more internal optical mirrors 437 and 439 (see FIG. 3) disposed within enclosure 431 and positioned at desired angles, one or more apertures 441 and 443 (see FIGS. 1 and 2) formed in the walls of enclosure 431, and various types of lenses (not shown) if needed. The input end of input bus IB is connected to fitting 433, and the output end of output bus OB is connected to fitting 435. As best illustrated in FIG. 3, a source signal from light source 210 enters enclosure 431 through aperture 441 (see FIG. 1), is reflected off internal mirror 437, and is diverted into input bus IB. A return signal from output bus OB is reflected off internal mirror 439 and diverted toward signal receiving device 230 through aperture 443 (see FIG. 1).

Figure 11:
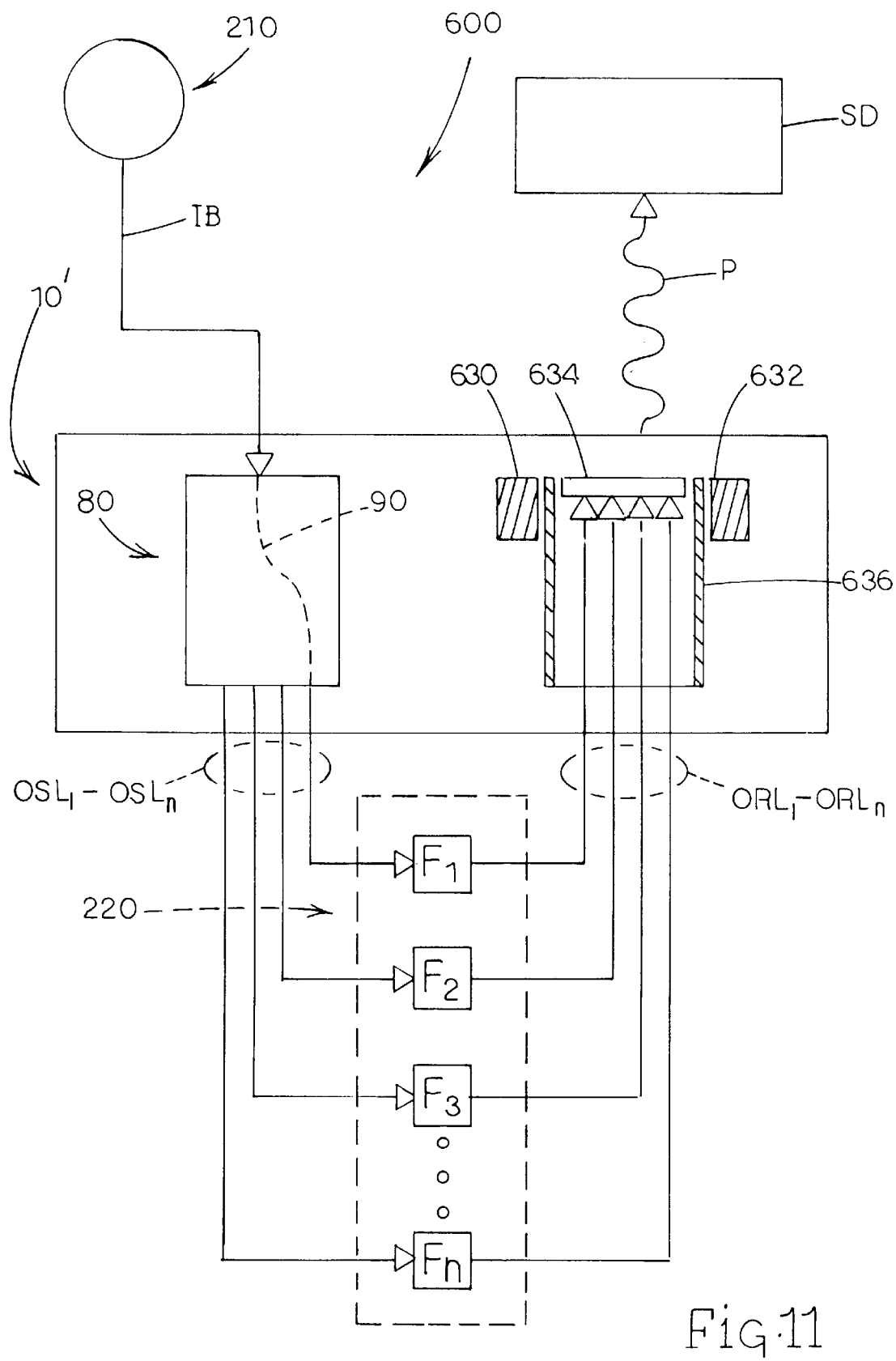
FIG. 11 is a schematic diagram of an analytical testing and data acquisition system provided in accordance with another embodiment of the present invention.
Figure 12A:
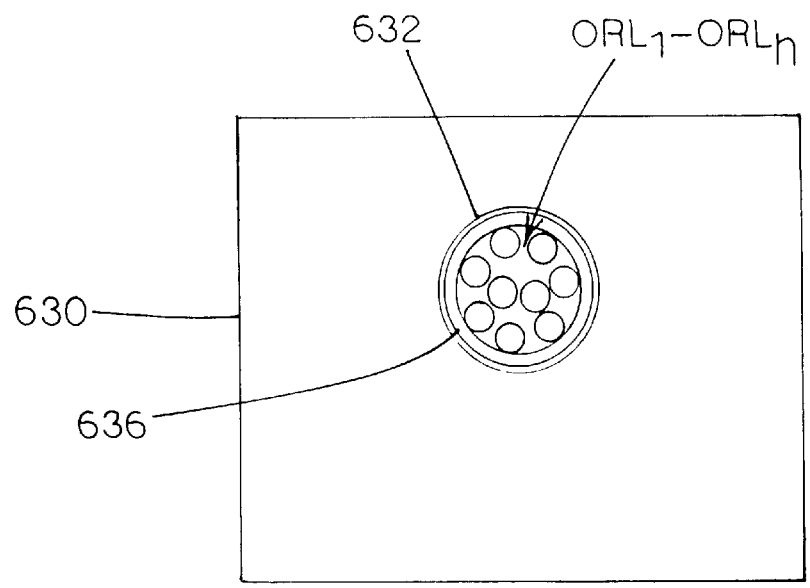
FIG. 12A is a front elevation view of a fiber-optic bundle mounting component provided with the apparatus illustrated in FIG. 11.
Figure 12B:
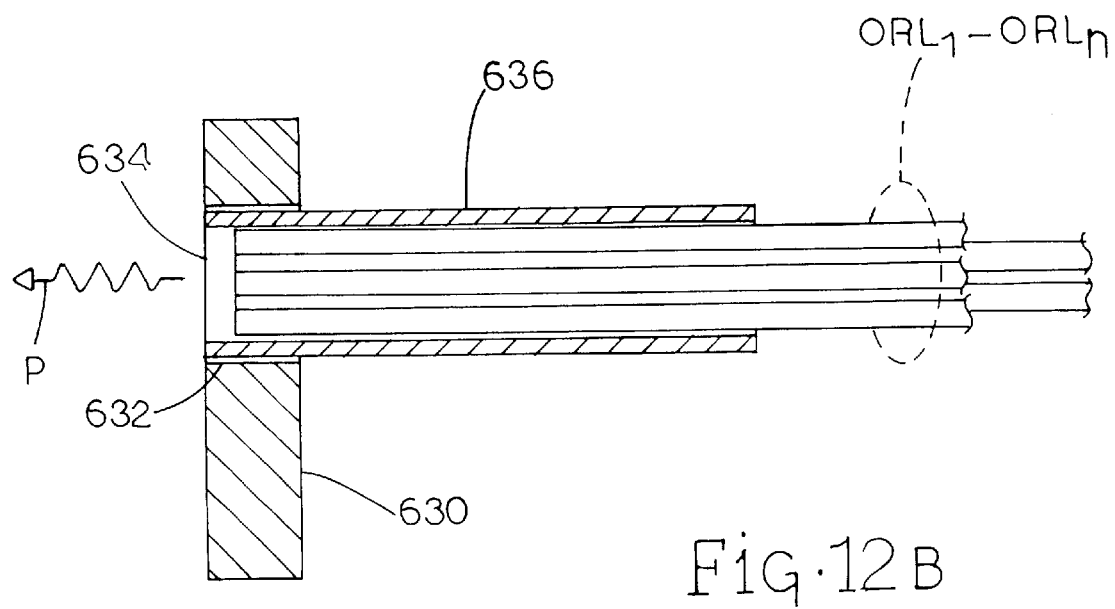
FIG. 12B is a cross-sectional side view of the mounting component illustrated in FIG. 12A.

Referring now to FIGS. 11, 12A, and 12B, another analytical testing and data acquisition system, generally designated 600, is illustrated according to another embodiment of the present invention. In some cases, it may be desirable to eliminate either the multiplexing or the demultiplexing feature of the invention. Accordingly, this embodiment provides an alternative multiplexing apparatus, generally designated 10', in which return line selector device 130 has been eliminated. Source line selector device 80 functions as described hereinabove. In the present embodiment, multiplexing apparatus 10' comprises an output bus mounting assembly 630. Output bus mounting assembly 630 includes an output aperture 632 in which a lens 634 is preferably disposed. Lens 634 can be situated at the terminal end of a cylindrical collar 636 or other suitable means for retaining and collecting optical return lines $ORL_1$–$ORL_n$ in a fixed-position bundle. In this embodiment, the bundle of optical return lines $ORL_1$–$ORL_n$ collected from, for example, aperture rows 16 or 18 (see FIGS. 2 and 3) is considered in effect to be a multi-channel output bus for analytical testing system 600. The bundle of optical return lines $ORL_1$–$ORL_n$ could also include an extra test line that is connected to a reference source. In FIG. 12A, for example, a total of nine lines are illustrated. For another example, a 16-channel system would have seventeen lines (again assuming one test line were included). Output aperture 632 is optically aligned with the receiving window of a sample detector SD or other similar analyzing device or light-receiving component thereof.

In operation, a sample beam from light source 210 is directed through input bus IB into the input side of source line selector device 80 in the manner described hereinabove. As also described hereinabove, source line selector device 80 is indexed by motor 40, shaft 42, gear wheels 45 and 47, and other associated components (see FIGS. 2 and 3) so as to select one of optical source lines $OSL_1$–$OSL_n$. The signal is transferred out from source line selector device 80 through the selected optical source line $OSL_1$–$OSL_n$ and associated fitting of one of aperture rows 16 and 18 to the selected sample container or other type of test site $F_1$–$F_n$ of encoding system 220. The transmitted light beam P is then returned through the corresponding one of optical return lines $ORL_1$–$ORL_n$, through one of aperture rows 16 or 18, to output bus mounting assembly 630 where all optical return lines $ORL_1$–$ORL_n$ are bundled at output aperture 632. Transmitted light beam P emanating from selected optical return line $ORL_1$–$ORL_n$ is directed into the window of sample detector SD. This window is large enough to receive light from any of the ends of optical return lines $ORL_1$–$ORL_n$ bundled at output bus mounting assembly 630. As an example, the window can be approximately 1 $cm^2$ in area, and the fiber ends of optical return lines $ORL_1$–$ORL_n$ can be positioned approximately 0.5 cm away from the window.

It will be noted that multiplexing apparatus 10', in which either source line selector device 80 or return line selector device 130 is eliminated, and either including or not including the other features of spectrophotometer 600, can be integrated into the various systems of the invention described with reference to FIGS. 3, 8 and 10 in the place of multiplexing apparatus 10.

It is therefore seen from the foregoing description that the present invention provides a number of systems, devices, and methods benefiting from the use of fiber-optics coupled with sample measurement systems. The embodiments described herein result in high-quality analysis and quantification of analytical samples with decreased effort, and enable the efficient and controlled selection and routing of optical signals and signal paths with minimal light loss.

It will be understood that the spectrophotometers described hereinabove are generally of the type involving the transmission measurement of a sample, wherein a light beam passes through a sample cell or flow cell containing the sample to be analyzed. The invention, however, is equally applicable to spectrophotometers of the type in which the sample to be analyzed is subjected to reflectance measurement and consequently do not necessarily require a sample cell or flow cell for operation.

It will be understood that the embodiments described hereinabove can be modified without undue effort to utilize more than one multiplexing apparatus 10 or 10', light source 210, signal receiving device 230 or SD, and/or set F of sample measurement components.

It will be further understood that various details of the invention may be changed without departing from the scope of the invention. Furthermore, the foregoing description is for the purpose of illustration only, and not for the purpose of limitation-the invention being defined by the claims.

What is claimed is:

1. A sample measuring and analysis system comprising:
   (a) an optical channel selecting apparatus comprising:
      (i) an optical input selection device defining a first optical path, the first optical path running between a first input end and a first output end, and the first output end rotatable about a first central axis to a plurality of first index positions defined along a first circular path;
      (ii) an optical output selection device defining a second optical path, the second optical path running between a second input end and a second output end, and the second input end rotatable about a second central avis oriented in non-collinear relation to the first central axis to a plurality of second index positions defined along a second circular path; and
      (iii) a controller element communicating with the optical input selection device and the optical output selection device for selectively aligning the first optical path with the first index positions and the second optical path with the second index positions;
   (b) a plurality of optical source lines corresponding to the plurality of first index positions and selectively communicating with the first optical path;
   (c) a plurality of optical return lines corresponding to the plurality of second index positions and selectively communicating with the second optical path; and
   (d) an optical signal receiving device optically communicating with the second output end.

2. The system according to claim 1 wherein the optical input selection device comprises:
   (a) a first rotary element rotatable about the first central axis, the first rotary element comprising a first input surface and an opposing first output surface, wherein the first input end is exposed at the first input surface and the first output end is exposed at the first output surface; and (b) a first stationary element disposed adjacent to the first output surface and having a plurality of circumferentially spaced first stationary element apertures, wherein each first stationary element aperture is disposed in alignment with the first circular path.

3. The system according to claim 2 wherein the optical output selection device comprises:
   (a) a second rotary element rotatable about the second central axis, the second rotary element comprising a second input surface and an opposing second output surface, wherein the second input end is exposed at the second input surface and the second output end is exposed at the second output surface; and
   (b) a second stationary element disposed adjacent to the second input surface and having a plurality of circumferentially spaced second stationary element apertures, wherein each second stationary element aperture is disposed in alignment with the second circular path.

4. The system according to claim 1 wherein the first optical path is defined by a first internal optical fiber disposed within the optical input selection device and extending between the first input end and the first output end.

5. The system according to claim 4 wherein the second optical path is defined by a second internal optical fiber disposed within the optical output selection device and extending between the second input end and the second output end.

6. The system according to claim 1 wherein the controller element comprises a rotatable coupling mechanism interconnecting the optical input selection device and the optical output selection device, wherein rotation of the coupling mechanism causes synchronized rotation of the first output end of the first optical path and the second input end of the second optical path.

7. The system according to claim 1 comprising a plurality of sample test sites, each sample test site optically communicating with a corresponding one of the optical source lines and a corresponding one of the optical return lines.

8. The system according to claim 1 comprising a light source optically coupled to the first input end.

9. The system according to claim 2 wherein the first rotary element comprises a lateral surface disposed between the first input surface and the first output surface, and the first stationary element comprises an annular section coaxially disposed about the lateral surface.

10. The system according to claim 9 comprising a bearing coaxially interposed between the lateral surface and the annular section.

11. The system according to claim 6 wherein the optical input selection device comprises a first set of teeth, the optical output selection device comprises a second set of teeth, and the coupling mechanism comprises a gear engaging the first and second sets of teeth.

12. A sample measurement anti analysis system comprising:
   (a) a fiber-optic channel selecting apparatus comprising:
      (i) an optical input selection device rotatable about a first central axis and comprising a first rotary element having a first internal bore and a first internal optical fiber extending through the first internal bore, the first internal optical fiber having a first input end and a first output end, the first input end disposed collinearly with the first central axis and the first output end disposed at a radially offset distance from the first central axis;
      (ii) an optical output selection device rotatable about a second central axis and comprising a second rotary element having a second internal bore and a second internal optical fiber extending through the second internal bore, the second internal optical fiber having a second input end and a second output end, the second input and disposed at a radially offset distance from the second central axis and the second output end disposed collinearly with the second central axis; and
      (iii) a rotatable coupling mechanism interconnecting the optical input selection device and the optical output selection device, wherein rotation of the coupling mechanism causes rotation of the first output end and the second input end;
   (b) a plurality of optical source lines having respective source line input ends, each source line input end selectively optically alignable with the first output end;
   (c) a plurality of optical return lines having respective return line output ends, each return line output end selectively optically alignable with the second input end; and
   (d) an optical signal receiving device optically communicating with the second output end.

13. The system according to claim 12 wherein:
   (a) the first rotary element comprises a first input end surface and an opposing first output end surface, the first input end of the first internal optical fiber is exposed at the first input end surface, and the first output end of the first internal optical fiber is exposed at the first output end surface; and
   (b) the optical input selection device comprises a first stationary element disposed adjacent to the first output end surface and having a plurality of circumferentially spaced first stationary element apertures, wherein each first stationary element aperture is disposed at the radially offset distance from the first central axis, and the first output end of the first internal optical fiber is alignable with a selected one of the first stationary element apertures through rotation of the first rotary element.

14. The system according to claim 13 wherein:
   (a) the second rotary element comprises a second input end surface and an opposing second output end surface, the second input end of the second internal optical fiber is exposed at the second input end surface, and the second output end of the second internal optical fiber is exposed at the second output end surface; and
   (b) the optical output selection device comprises second stationary element disposed adjacent to the second input end surface and having a plurality of circumferentially spaced second stationary element apertures, wherein each second stationary element aperture is disposed at the radially offset distance from the second central axis, and the second input end of the second internal optical fiber is alignable with a selected one of the second stationary element apertures through rotation of the second rotary element.

15. The system according to claim 12 comprising a light source optically coupled to the first input end.

16. The system according to claim 12 comprising a plurality of sample test sites, each sample test site optically communicating with a respective optical source line and a corresponding optical return line.

17. The system according to claim 12 wherein the optical input selection device comprises a first set of teeth, the optical output selection device comprises a second set of teeth, and the coupling mechanism comprises a gear engaging the first and second sets of teeth.

18. The system according to claim 12 wherein the first central axis is oriented in a non-collinear relation to the second central axis.

19. The system according to claim 13 wherein the first rotary element comprises a lateral surface disposed between the first input end surface and the first output end surface, and the first stationary element comprises a annular section coaxially disposed about the lateral surface.

20. The system according to claim 19 comprising a bearing coaxially interposed between the lateral surface and the annular section.

21. A sample measurement and analysis system comprising:
- (a) a fiber-optic channel selecting apparatus comprising a rotary element rotatable about a central axis and having an internal bore, and an internal optical fiber extending through the internal bore, the internal optical fiber having an internal optical fiber input end and an internal optical fiber output end, the internal optical fiber input end disposed collinearly with the central axis and the internal optical fiber output end disposed at a radially offset distance from the central axis;
- (b) a plurality of optical source lines having respective source line input ends, each source line input end selectively optically alignable with the internal optical fiber output end;
- (c) a plurality of optical return lines terminating at respective optical fiber ends;
- (d) a mounting member supporting the optical fiber ends; and
- (e) an optical signal receiving device optically aligned with each optical fiber end.

22. The system according to claim 21 wherein:
- (a) the rotary element comprises an input end surface and an opposing output end surface, the internal optical fiber input end is exposed at the input end surface, and the internal optical fiber output end is exposed at the output end surface; and
- (b) the fiber-optic channel selecting apparatus comprises a stationary element disposed adjacent to the output end surface and having a plurality of circumferentially spaced stationary element apertures, each stationary element aperture is disposed at the radially offset distance from the central axis, and the internal optical fiber output end is alignable with a selected one of the stationary element apertures through rotation of the rotary element.

23. The system according to claim 21 comprising a plurality of sample test sites, each sample test site optically communicating with a corresponding one of the optical source lines and a corresponding one of the optical return lines.

24. The system according to claim 21 comprising a light source optically coupled to the internal optical fiber input end.

25. The system according to claim 21 comprising a gear coupled to the rotary element.

26. The system according to claim 22 wherein the rotary element comprises a lateral surface disposed between the input end surface and output end surface, and the stationary element comprises an annular section coaxially disposed about the lateral surface.

27. The system according to claim 26 comprising a bearing coaxially interposed between the lateral surface and the annular section.

28. A sample measuring and analysis system comprising:
- (a) an optical channel selection device comprising a rotary element rotatable about a central axis, the rotary element comprising an input end surface and an output end surface and having an internal bore defining an optical path running between the input end surface and the output end surface, the internal bore having a first bore end disposed at the input end surface collinearly with the central axis and a second bore end disposed at the output end surface and at a radially offset distance from the central axis, wherein the optical path is adjustable to a plurality of input channel positions;
- (b) a plurality of optical source lines, each source line corresponding to a respective input channel position and selectively coupled to the optical path;
- (c) a plurality of optical probes, each probe coupled to a respective source line; and
- (d) a plurality of optical return lines, each return line coupled to a respective probe.

29. The system according to claim 28 wherein each probe comprises a light-reflective member and a detection area adjacent to the light-reflective member for admitting a sample, and the source line and return line corresponding to the probe extend into the probe generally along the same direction and terminate at a side of the detection area generally opposite to the light-reflective member.

30. The system according to claim 28 wherein the optical channel selection device comprises a stationary element disposed adjacent to the output end and having a plurality of circumferentially spaced stationary element apertures, each stationary element aperture is disposed at the radially offset distance from the central axis, and the optical path is alignable with a selected one of the stationary element apertures at the output end through rotation of the rotary element.

31. The system according to claim 30 wherein the rotary element comprises a lateral surface disposed between the input end and output end, and the stationary element comprises an annular section coaxially disposed about the lateral surface.

32. The system according to claim 31 comprising a bearing coaxially interposed between the lateral surface and the annular section.

33. The system according to claim 28 comprising a gear coupled to the rotary element.

34. A method for acquiring data from samples, comprising the steps of:
- (a) selecting a test site from a plurality of available test sites by rotating a barrel about a central axis to selected channel position, the barrel comprising an internal bore and an internal optical fiber extending though the bore, the optical fiber having a fiber input end disposed collinearly with the central axis and a fiber output end disposed at a radially offset distance from the central axis, whereby rotation of the barrel to the selected channel position optically aligns the fiber output end with an optical source line optically communicating with the selected test site;
- (b) transmitting an optical signal through the internal optical fiber and source line to the selected test site to irradiate a sample disposed at the selected test site, whereby the optical signal is attenuated; and
- (c) transmitting the attenuated optical signal through an optical return line optically communicating with the selected test site.

35. The method according to claim 34 comprising the steps of:
  (a) selecting a next test site from the plurality of test sites by rotating the barrel to a next channel position, whereby the fiber output end becomes aligned with a next source line communicating with the next test site; and
  (b) sending an optical signal through the optical fiber and next source line to the next test site to irradiate a next sample disposed at the next test site, whereby an attenuated optical signal is emitted from the next test site and travels through a next return line communicating with the next test site.

36. The method according to claim 34 wherein selecting the test site brings the return line into communication with an optical receiving device.

37. The method according to claim 34 wherein the return line is one of a plurality of available return lines, each return line communicating with a respective test site and having an output end fixed in alignment with an optical receiving device, and transmitting the attenuated optical signal through the return line communicating with the selected test site enables the optical receiving device to receive the signal without having to adjust an optical path between the selected test site and the optical receiving device.

* * * * *

UNITED STATES PATENT AND TRADEMARK OFFICE
CERTIFICATE OF CORRECTION

PATENT NO.     : 6,661,512 B2
DATED          : December 9, 2003
INVENTOR(S)    : CJ Anthony Fernando and James E. Swon It is certified that error appears in the above-identified patent and that said Letters Patent is hereby corrected as shown below:

Column 24,
Line 44, change the word "avis" to -- axis --.

Column 25,
Line 54, change the word "anti" to -- and --.

Signed and Sealed this

Thirteenth Day of July, 2004

JON W. DUDAS
*Acting Director of the United States Patent and Trademark Office*